(12) United States Patent
Ito et al.

(10) Patent No.: US 8,563,969 B2
(45) Date of Patent: Oct. 22, 2013

(54) BENZANTHRACENE COMPOUND AND ORGANIC ELECTROLUMINESCENCE DEVICE USING THE SAME

(75) Inventors: Mitsunori Ito, Sodegaura (JP); Masahiro Kawamura, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 396 days.

(21) Appl. No.: 12/809,541

(22) PCT Filed: Dec. 12, 2008

(86) PCT No.: PCT/JP2008/072688
§ 371 (c)(1),
(2), (4) Date: Jul. 29, 2010

(87) PCT Pub. No.: WO2009/081776
PCT Pub. Date: Jul. 2, 2009

(65) Prior Publication Data
US 2011/0297918 A1    Dec. 8, 2011

(30) Foreign Application Priority Data
Dec. 20, 2007    (JP) .................................. 2007-329354

(51) Int. Cl.
*H01L 29/08*    (2006.01)
(52) U.S. Cl.
USPC ........... 257/40; 585/26; 585/27; 257/E51.018
(58) Field of Classification Search
USPC ..................... 257/40, E51.018; 585/26–27
See application file for complete search history.

(56) References Cited

U.S. PATENT DOCUMENTS

| 2004/0214035 A1 | 10/2004 | Ikeda et al. |
| 2007/0228941 A1* | 10/2007 | Abe et al. ..................... 313/504 |
| 2007/0273272 A1 | 11/2007 | Kubota |

FOREIGN PATENT DOCUMENTS

JP    2000-178548 A    6/2000
(Continued)

OTHER PUBLICATIONS

Seliger et al., "Chemical Production of Excited States. Chemiluminescence of Carcinogenic Hydrocarbons Accompanying Their Metabolic Hydroxylation and a Proposal for Common Active Site Geometries for Hydroxylation", The Journal of Physical Chemistry, 1976, vol. 80(20), pp. 2296-2306.

(Continued)

*Primary Examiner* — Eugene Lee
*Assistant Examiner* — Elias M Ullah
(74) *Attorney, Agent, or Firm* — Foley & Lardner LLP

(57) ABSTRACT

A compound having the structure represented by the following formula (1) or (1)' as at least a part:

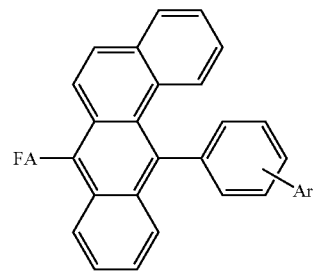

(1)

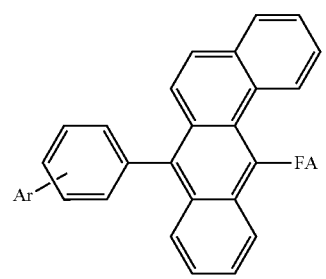

(1)' wherein FA is a fused aromatic ring, and Ar is an aromatic group.

4 Claims, 1 Drawing Sheet

(56) References Cited

FOREIGN PATENT DOCUMENTS

| | | |
|---|---|---|
| JP | 2001-335516 A | 12/2001 |
| JP | 2005-041843 A | 2/2005 |
| JP | 2007-277113 A | 10/2007 |
| JP | 2007-308477 A | 11/2007 |
| JP | 2008-063240 A | 3/2008 |
| JP | 2008-303365 A | 12/2008 |
| WO | WO 2008/145239 A2 | 12/2008 |

OTHER PUBLICATIONS

International Search Report mailing date of Jan. 13, 2009 for International Application No. PCT/JP2008/072688 with English International Preliminary Report on Patentability (9 pages).

* cited by examiner

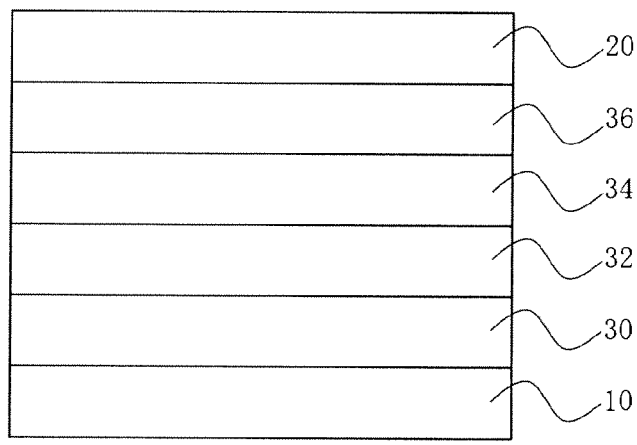

BENZANTHRACENE COMPOUND AND ORGANIC ELECTROLUMINESCENCE DEVICE USING THE SAME

TECHNICAL FIELD

The invention relates to a novel benzanthracene compound which is useful as an emitting material for an organic electroluminescence device, and an organic electroluminescence device using the same.

BACKGROUND ART

An organic electroluminescence (EL) device is a self-emission device utilizing the principle that a fluorescent compound emits light by the recombination energy of holes injected from an anode and electrons injected from a cathode when an electric field is impressed.

An organic EL device has made a remarkable progress. In addition, since an organic EL device has characteristics such as low voltage driving, high luminance, variety in emission wavelength, high response and capability of fabricating a thin and lightweight emitting device, its application to a wide range of fields is expected.

Emission materials used in an organic EL device have conventionally been studied actively since they influence largely the color of light emitted by a device or on emission life.

As the emission material, a material emitting light by itself and a host material containing a small amount of a dopant are known. Furthermore, it has been studied that triplet energy is used for emission by using a phosphorescent compound as an emission material instead of a fluorescent emitting material. By using such various emission materials, emission in a visible range from blue to red can be obtained.

As examples of the emitting material, Patent Documents 1 and 2 disclose benzanthracene derivatives. However, organic EL devices using these benzanthracene derivatives have short half life and are inferior in chromaticity.

[Patent Document 1] JP-A-2000-178548
[Patent Document 2] JP-A-2007-277113

An object of the invention is to provide a novel benzanthracene compound, an emitting material and an organic EL device using the emitting material.

DISCLOSURE OF THE INVENTION

According to the invention, the following compound, organic EL device and the like are provided.

1. A compound having the structure represented by the following formula (1) or (1)' as at least a part:

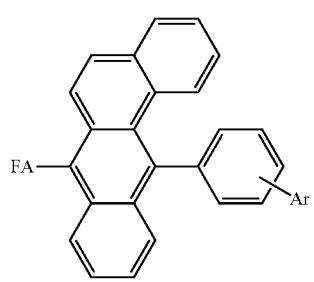

(1)

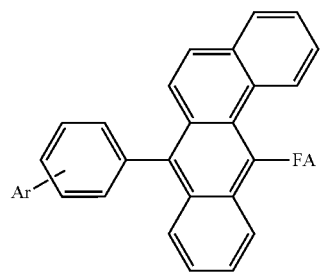

(1)' wherein FA is a fused aromatic ring, and Ar is an aromatic group.

2. A compound having the structure represented by the following formula (2) as at least a part:

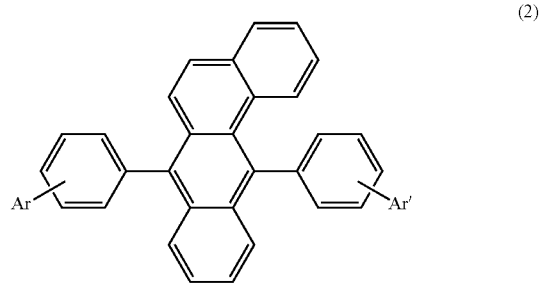

(2)

wherein Ar and Ar' are independently an aromatic group, and when Ar is the same as Ar', they are not rotationally symmetric about the central point of the benzanthracene skeleton, provided that the compound wherein both of Ar and Ar' are unsubstituted 2-naphthyl groups and bond to the p-position of the respective phenyl groups is excluded.

3. A compound having the structure represented by the following formula (3) as at least a part:

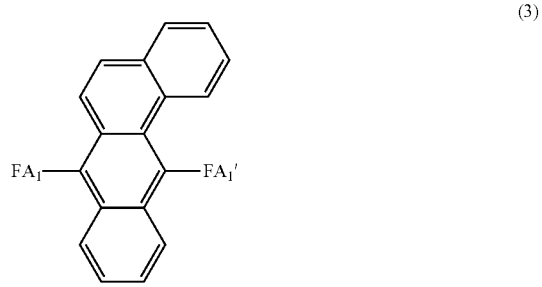

(3)

wherein $FA_1$ and $FA_1'$ are independently a bicyclic or tricyclic fused aromatic ring, and when $FA_1$ is the same as $FA_1'$, they are not rotationally symmetric about the central point of the benzanthracene skeleton, provided that the compound wherein both of $FA_1$ and $FA_1'$ are unsubstituted 2-naphthyl groups and the compound wherein both of $FA_1$ and $FA_1'$ are 9,9-dimethyl-2-fluorenyl groups are excluded.

4. An emitting material comprising the compound according to any one of 1 to 3.
5. An organic electroluminescence device which comprises:
   an anode, a cathode, and one or more organic thin film layers including an emitting layer, which are between the anode and the cathode,
   wherein at least one layer of the organic thin film layers comprises the compound according to any one of 1 to 3.

6. The organic electroluminescence device according to 5, wherein the layer comprising the compound further comprises at least one of a phosphorescent dopant and a fluorescent dopant.
7. The organic electroluminescence device according to 6, wherein the fluorescent dopant is at least one of arylamine compounds and styrylamine compounds.
8. The organic electroluminescence device according to 6 or 7, wherein the phosphorescent dopant is a metal complex.

According to the invention, a novel benzanthracene compound and an emitting material, and an organic EL device using the emitting material can be provided.

The organic EL device using the emitting material of the invention is superior in chromaticity and half life.

BRIEF DESCRIPTION OF THE DRAWINGS

FIG. 1 is a schematic cross-sectional view of the organic EL device according to one embodiment of the invention.

BEST MODE FOR CARRYING OUT THE INVENTION

The benzanthracene compound of the invention is a compound having one of the following structures (1), (1)', (2) and (3) as at least a part:

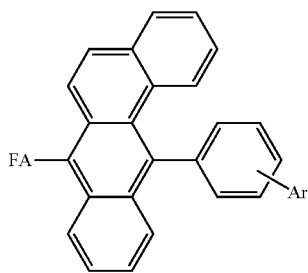

(1)

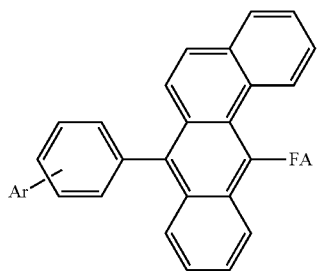

(1)' wherein FA is a fused aromatic ring, and Ar is an aromatic group;

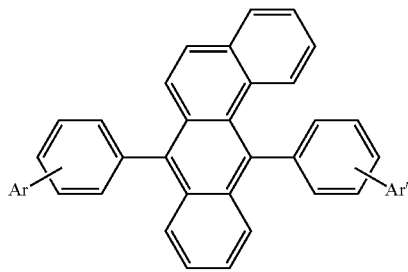

(2)

wherein Ar and Ar' are independently an aromatic group, and when Ar equals Ar', they are not rotationally symmetric about the central point of the benzanthracene skeleton, provided that the compound wherein both of Ar and Ar' are unsubstituted 2-naphthyl groups and bond to the para-position of the respective phenyl groups is excluded; and

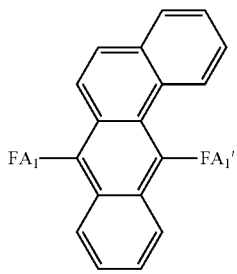

(3)

wherein $FA_1$ and $FA_1'$ are independently a bicyclic or tricyclic fused aromatic ring, and when $FA_1$ equals $FA_1'$, they are not rotationally symmetric about the central point of the benzanthracene skeleton, provided that the compound wherein both of $FA_1$ and $FA_1'$ are unsubstituted 2-naphthyl groups and the compound wherein both of $FA_1$ and $FA_1'$ are 9,9-dimethyl-2-fluorenyl groups are excluded.

The benzanthracene compound of the invention contains the above structure as a part or a whole. For example, the benzanthracene compound of the invention may be a compound in which the above structure is further substituted, and may be the structure itself.

The term "rotationally symmetric about (with respect to) the central point of the anthracene skeleton" means that when the formula of a compound is rotated on the paper at an angle of 180° about the central point of the anthracene skeleton of the benzanthracene skeleton, rotational symmetry is approved, as shown by the formulas (2a) and (2b), for example. The compound shown by the formula (2c) is not rotationally symmetric about the central point of the anthracene skeleton of the benzanthracene skeleton.

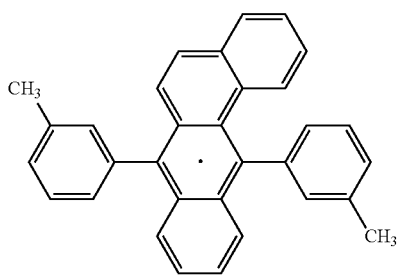

(2a)

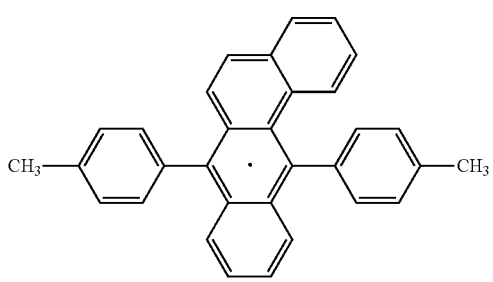

(2b)

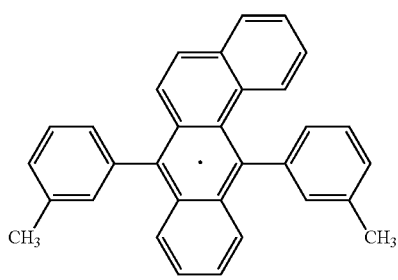

(2c)

The above-mentioned aromatic group for Ar and Ar' preferably has 6 to 60 (preferably 6 to 30) ring carbon atoms that form a ring (hereinafter referred to as "ring carbon atoms"). Examples thereof include a phenyl group, an indenyl group, a fluorenyl group, a naphthyl group, an anthryl group, a phenanthryl group, a naphthacenyl group, an acenaphthylenyl group, a biphenylenyl group, a chrysenyl group, a pyrenyl group, a triphenylenyl group, a fluoranthenyl group and a perylenyl group. A naphthyl group, a phenanthryl group, a chrysenyl group, a pyrenyl group, a triphenylenyl group, a fluorenyl group, a biphenyl group and a terphenyl group are preferred. Specific examples include a phenyl group, a 6-indenyl group, a 7-indenyl group, a 1-fluorenyl group, a 2-fluorenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 3-acenaphthylenyl group, a 4-acenaphthylenyl group, a 1-biphenylenyl group, a 2-biphenylenyl group, a 1-chrysenyl group, a 2-chrysenyl group, a 3-chrysenyl group, a 6-chrysenyl group, a 1-pyrenyl group, a 2-pyrenyl group, a 4-pyrenyl group, a 1-triphenylenyl group, a 2-triphenylenyl group, a 1-fluoranthenyl group, a 2-fluoranthenyl group, a 3-fluoranthenyl group, a 7-fluoranthenyl group, a 8-fluoranthenyl group, a 1-perylenyl group, a 2-perylenyl group, a 3-perylenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a 2-dibenzofuryl group, a 3-dibenzofuryl group, a 4-dibenzofuryl group, a 2-dibenzothienyl group, a 3-dibenzothienyl group, a 4-dibenzothienyl group and a fluorenyl group.

Preferred are a phenyl group, a 1-naphthyl group, a 2-naphthyl group, a 9-phenanthryl group, a 2-phenanthryl group, a 2-dibenzofuryl group and a 4-dibenzofuryl group.

The above-mentioned fused aromatic ring for FA, and the bicyclic or tricyclic fused aromatic ring for $FA_1$ and $FA_1'$ preferably have 10 to 18 ring carbon atoms. Examples of the fused aromatic rings include an indenyl group, a fluorenyl group, a naphthyl group, an anthryl group, a phenanthryl group, an acenaphthylenyl group and a biphenylenyl group. A naphthyl group and a phenanthryl group are preferable.

Specific examples include a 6-indenyl group, a 7-indenyl group, a 1-fluorenyl group, a 2-fluorenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 3-acenaphthylenyl group, a 4-acenaphthylenyl group, a 1-biphenylenyl group and a 2-biphenylenyl group.

The above-mentioned fused aromatic rings for FA, $FA_1$ and $FA_1'$ are preferably a fused ring wherein two or three 6-membered and 5-membered rings are fused, and particularly preferably naphthyl and phenanthryl. In the benzanthracene derivative of the invention, these fused rings may be substituted. Examples of the substituent include an alkyl group having 1 to 6 carbon atoms, an aromatic group having 6 to 60 carbon atoms and a heterocyclic group having 2 to 60 carbon atoms.

Substituents of the structures of the above formulas (1), (1)', (2) and (3) include an alkyl group (one having preferably 1 to 20, more preferably 1 to 12 and particularly preferably 1 to 8 carbon atoms, the specific examples of which include methyl, ethyl, isopropyl, t-butyl, n-octyl, n-decyl, n-hexadecyl, cyclopropyl, cyclopentyl and cyclohexyl), an alkenyl group (one having preferably 2 to 20, more preferably 2 to 12 and particularly preferably 2 to 8 carbon atoms, the specific examples of which include vinyl, allyl, 2-butenyl and 3-pentenyl), an alkynyl group (one having preferably 2 to 20, more preferably 2 to 12 and particularly preferably 2 to 8 carbon atoms, the specific examples of which include propynyl and 3-pentynyl), an aryl group (one having preferably 6 to 60, more preferably 6 to 30, particularly preferably 6 to 20 carbon atoms, the specific examples of which include phenyl, fluorenyl, naphthyl, anthryl, phenanthryl, chrysenyl, pyrenyl, triphenylenyl and fluoranthenyl), a substituted or unsubstituted amino group (one having preferably 0 to 20, more preferably 0 to 12 and particularly preferably 0 to 6 carbon atoms, the specific examples of which include amino, methylamino, dimethylamino, diethylamino, diphenylamino and dibenzylamino), an alkoxy group (one having preferably 1 to 20, more preferably 1 to 12 and particularly preferably 1 to 8 carbon atoms, the specific examples of which include methoxy, ethoxy and buthoxy), an aryloxy group (one having preferably 6 to 20, more preferably 6 to 16 and particularly preferably 6 to 12 carbon atoms, the specific examples of which include phenyloxy and 2-naphthyloxy), an acyl group (one having preferably 1 to 20, more preferably 1 to 16 and particularly preferably 1 to 12 carbon atoms, the specific examples of which include acetyl, benzoyl, formyl and pivaloyl), an alkoxycarbonyl group (one having preferably 2 to 20, more preferably 2 to 16 and particularly preferably 2 to 12 carbon atoms, the specific examples of which include methoxycarbonyl and ethoxycarbonyl), an aryloxycarbonyl group (one having preferably 7 to 20, more preferably 7 to 16 and particularly preferably 7 to 10 carbon atoms, the specific examples of which include phenyloxycarbonyl), an acyloxy group (one having preferably 2 to 20, more preferably 2 to 16 and particularly preferably 2 to 10 carbon atoms, the specific examples of which include acetoxy and benzoyloxy), an acylamino group (one having preferably 2 to 20, more preferably 2 to 16 and particularly preferably 2 to 10 carbon atoms, the specific examples of which include acetylamino and benzoylamino), an alkoxycarbonylamino group (one having preferably 2 to 20, more preferably 2 to 16 and particularly preferably 2 to 12 carbon atoms, the specific examples of which include methoxycarbonylamino), an aryloxycarbonylamino group (one having preferably 7 to 20, more preferably 7 to 16 and particularly preferably 7 to 12 carbon atoms, the specific examples of which include phenyloxycarbonylamino), a substituted or unsubstituted sulfonylamino group (one having preferably 1 to 20, more preferably 1 to 16 and particularly preferably 1 to 12 carbon atoms, the specific examples of which include methanesulfonylamino and benzenesulfonylamino), a substituted or unsubstituted sulfamoyl group (one having preferably 0 to 20, more preferably 0 to 16 and particularly preferably 0 to 12 carbon atoms, the specific examples of which include sulfamoyl, methylsulfamoyl, dimethylsulfamoyl and phenylsulfamoyl), a substituted or unsubstituted carbamoyl group (one having preferably 1 to 20, more preferably 1 to 16 and particularly preferably 1 to 12 carbon atoms, the specific examples of which include carbamoyl, methylcarbamoyl, diethylcarbamoyl and phenylcarbamoyl), an alkylthio group (one having preferably 1 to 20, more preferably 1 to 16 and particularly preferably 1 to 12 carbon atoms, the specific examples of which include methylthio and ethylthio), an arylthio group (one having preferably 6 to 20, more preferably 6 to 16 and particularly preferably 6 to 12 carbon atoms, the specific examples of which include phenylthio), a substituted or unsubstituted sulfonyl group (one having preferably 1 to 20, more preferably 1 to 16 and particularly preferably 1 to 12 carbon atoms, the specific examples of which include mesyl and tosyl), a substituted or unsubstituted sulfinyl group (one having preferably 1 to 20, more preferably 1 to 16 and particularly preferably 1 to 12 carbon atoms, the specific examples of which include methanesulfinyl and benzenesulfinyl), a substituted or unsubstituted ureido group (one having preferably 1 to 20, more preferably 1 to 16 and particularly preferably 1 to 12 carbon atoms, the specific examples of which include ureido, methylureido and phenylureido), a substituted or unsubstituted phosphoric amide group (one having preferably 1 to 20, more preferably 1 to 16 and particularly preferably 1 to 12 carbon atoms, the specific examples of which include diethylphosphoric amide and phenylphosphoric amide), a hydroxyl group, a mercapto group, a halogen atom (for example, a fluorine atom, a chlorine atom, a bromine atom and an iodine atom), a cyano group, a sulfo group, a carboxy group, a nitro group, a hydroxamic acid group, a sulfino group, a hydrazino group, an imino group, a heterocyclic group (one having preferably 1 to 30 and more preferably 1 to 12 carbon atoms and containing, as the hetero atom, a nitrogen atom, an oxygen atom and a sulfur atom, for example, the specific examples of which include imidazolyl, pyridyl, quinolyl, furyl, thienyl, piperidyl, morpholino, benzoxazolyl, benzimidazolyl, benzothiazolyl and carbazolyl), and a silyl group (one having preferably 3 to 40, more preferably 3 to 30 and particularly preferably 3 to 24 carbon atoms, the examples of which include trimethylsilyl and triphenylsilyl). These substituents may be further substituted. If there are two or more substituents, these substituents may be the same or different. If possible, they may be combined each other to form a ring.

Examples of preferable substituents include methyl, ethyl, propyl, isopropyl, butyl, sec-butyl, tert-butyl, cyclohexyl, phenyl, 1-naphthyl, 2-naphthyl, trimethylsilyl and triphenylsilyl.

Examples of the compounds represented by the formulas (1), (1)', (2) and (3) are shown below:

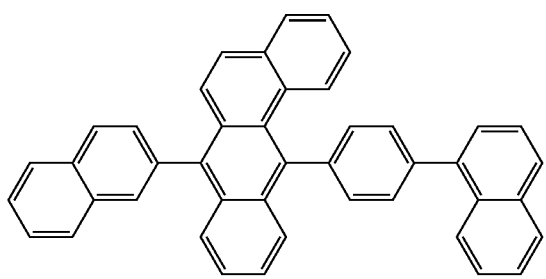

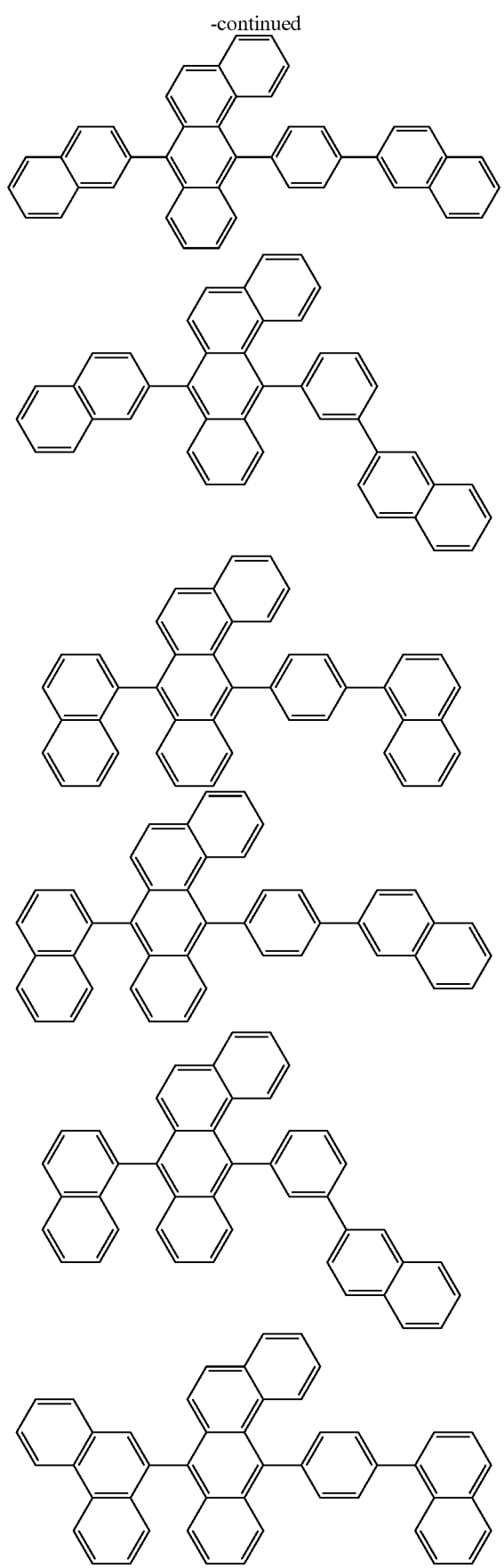

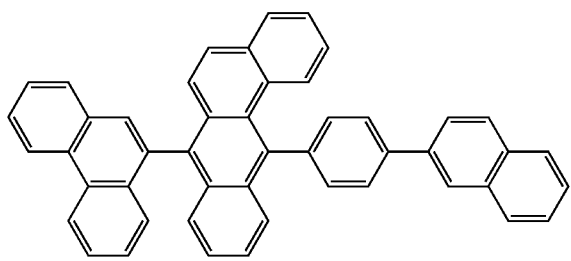
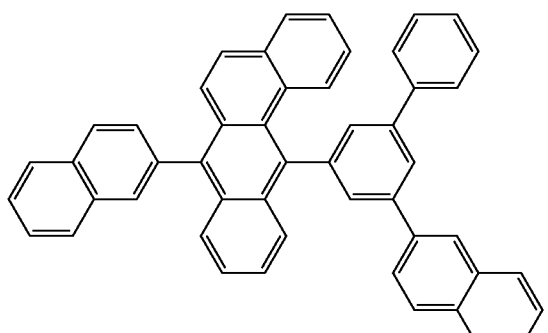
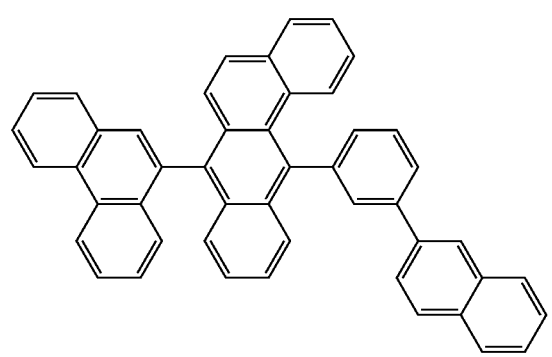
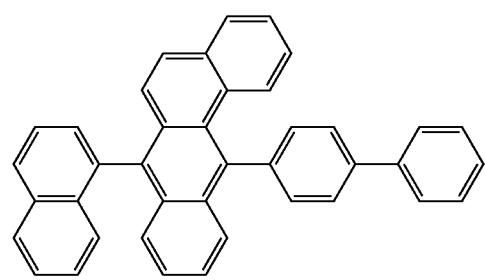
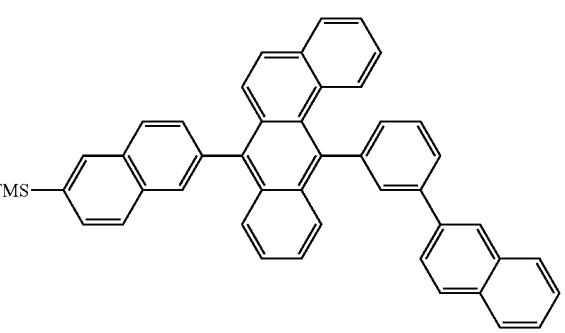
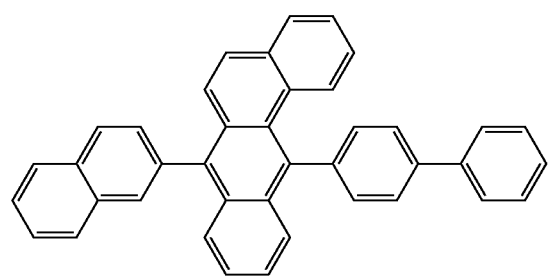
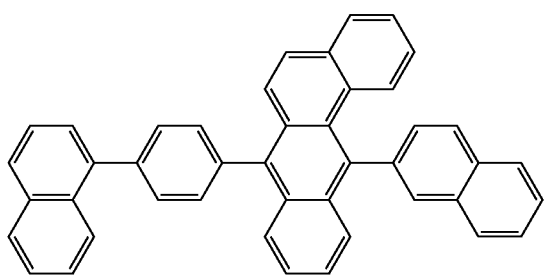
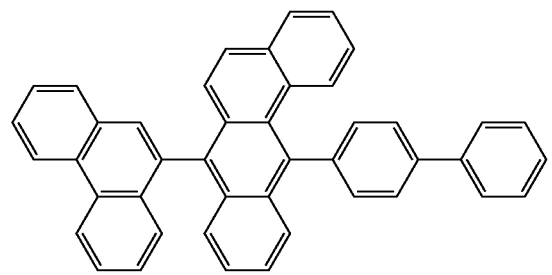
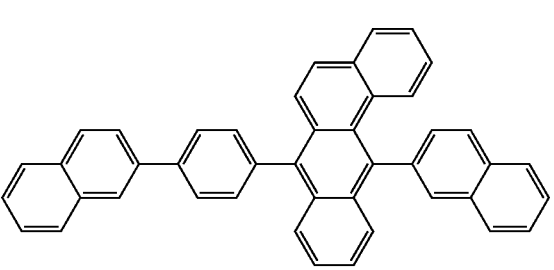

-continued
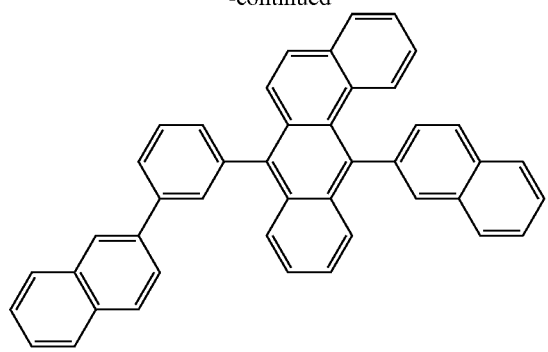
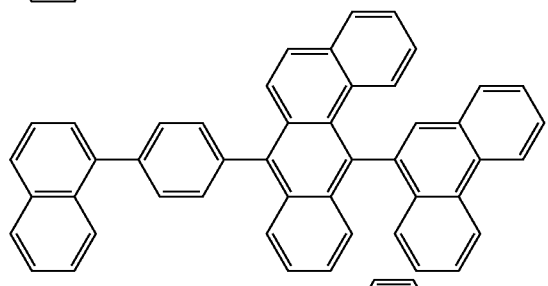
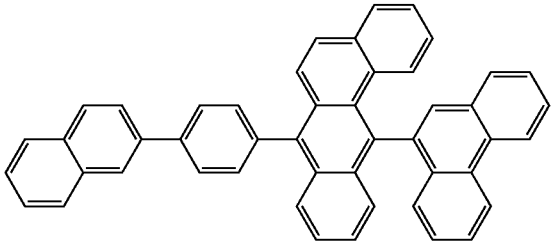
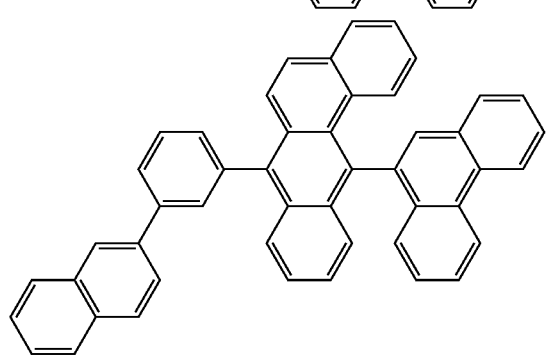
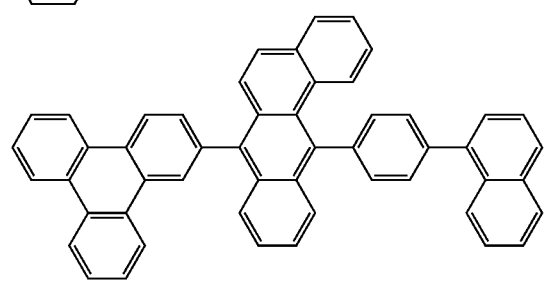
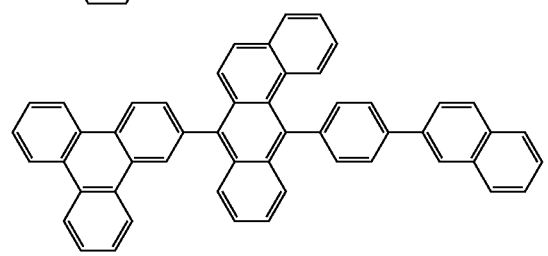
-continued
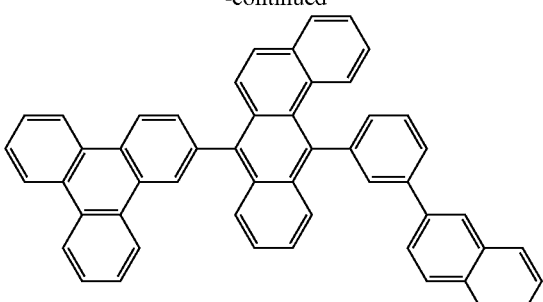
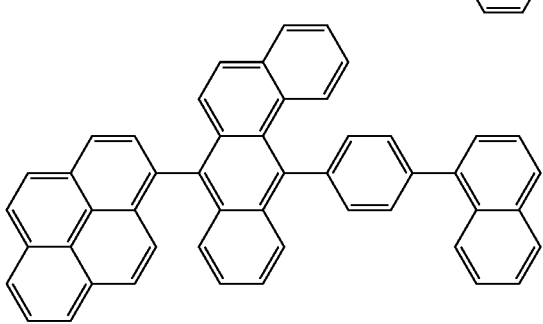
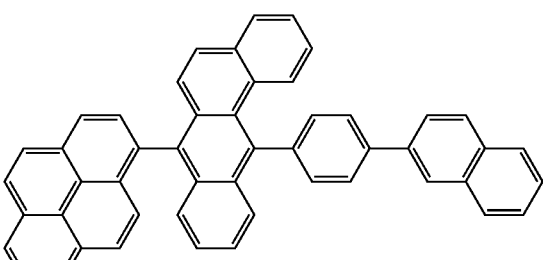
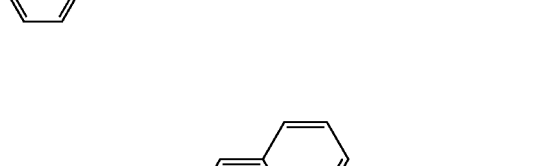
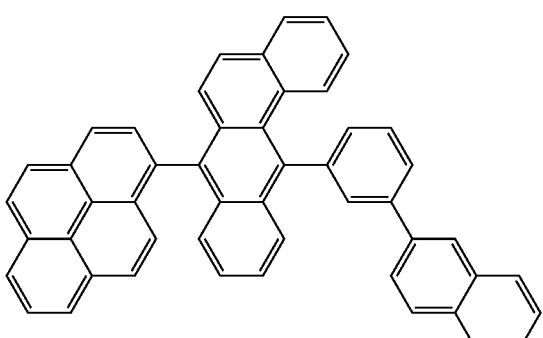
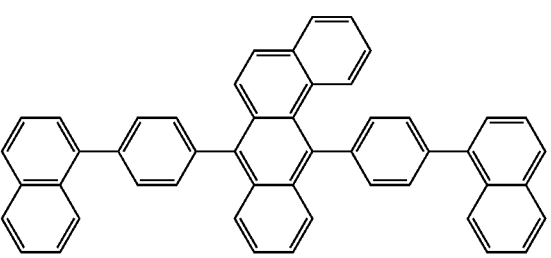

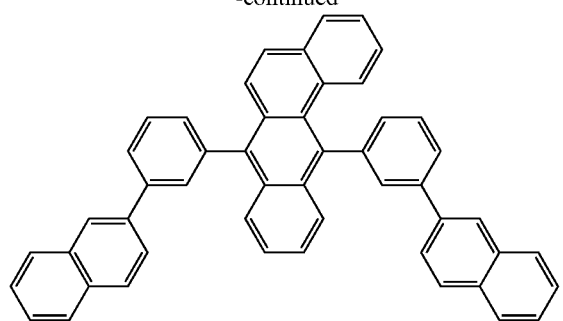
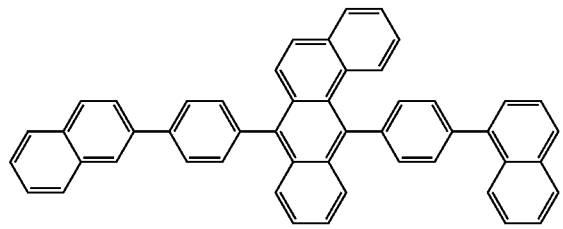
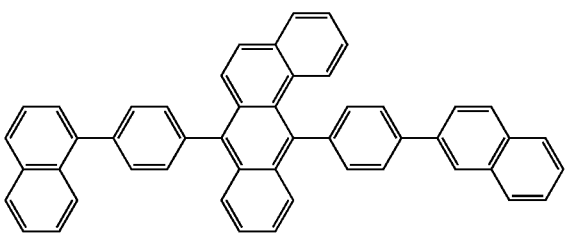
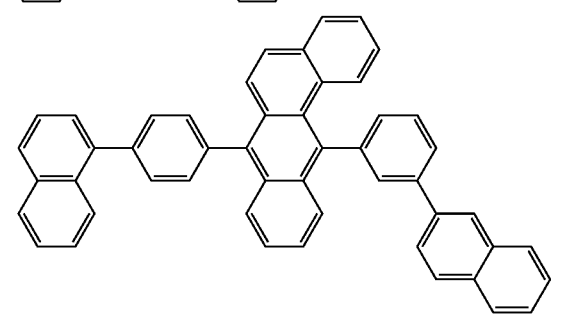
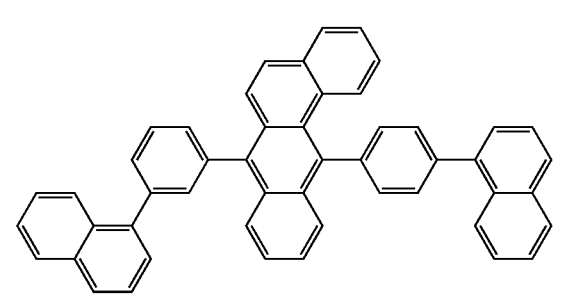
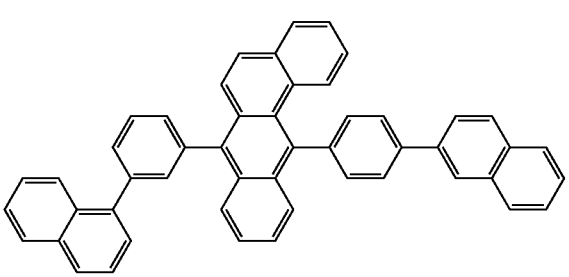
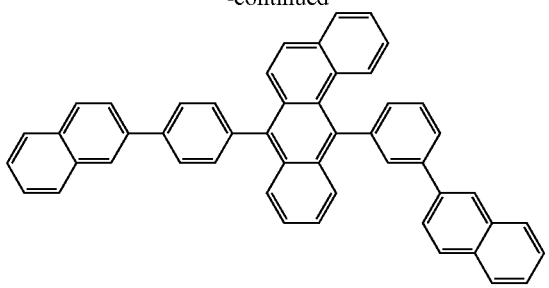
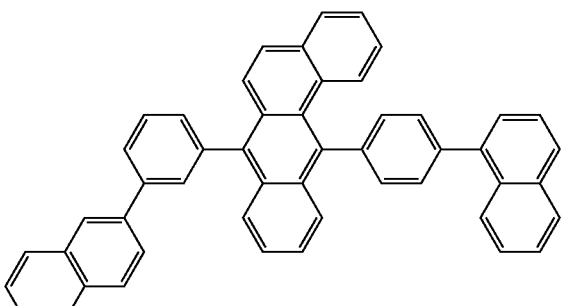
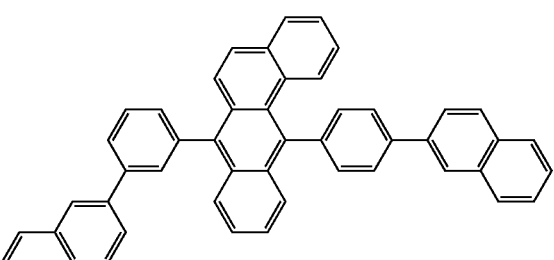
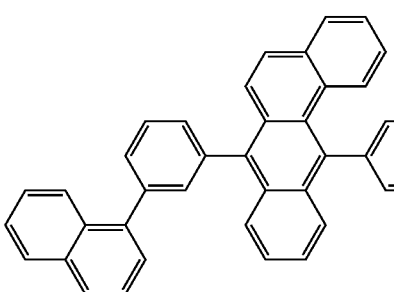
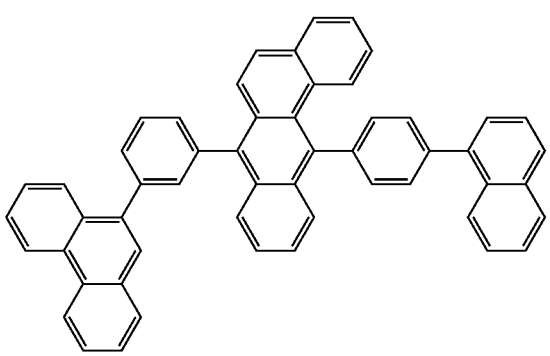

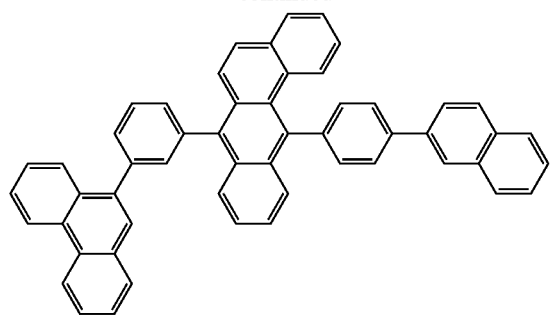
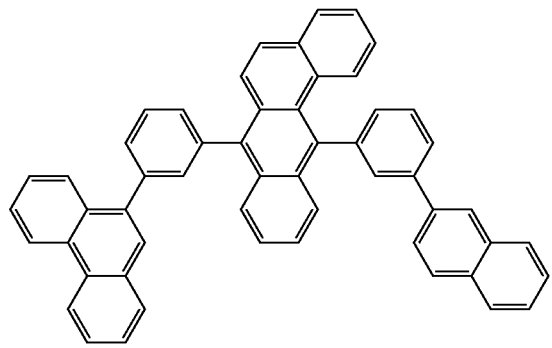
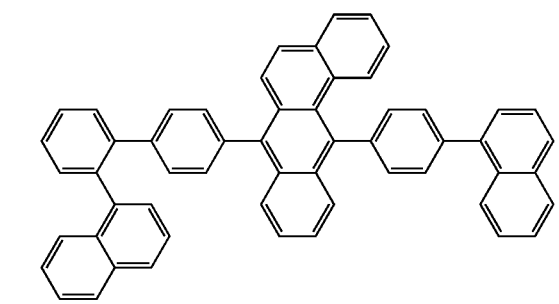
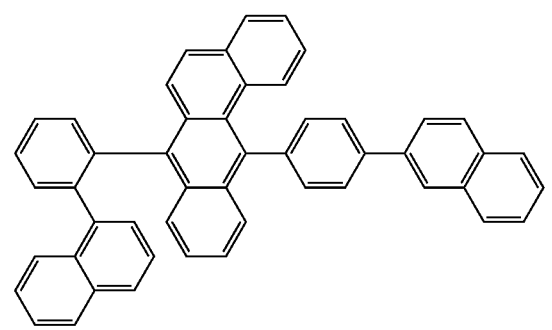
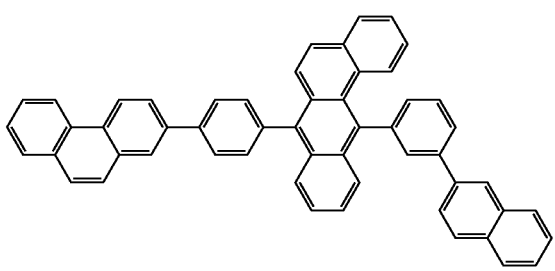
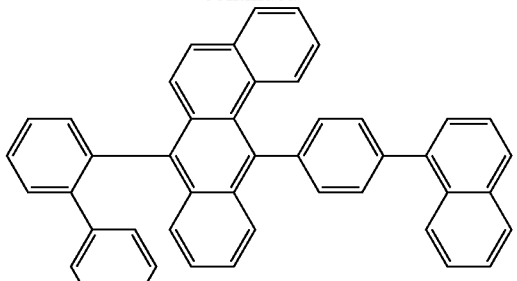
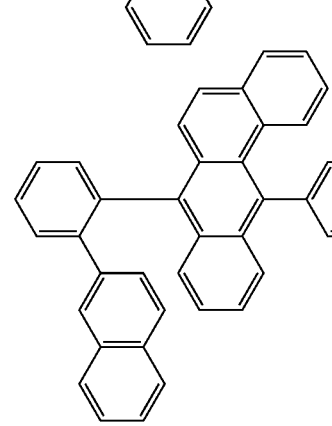
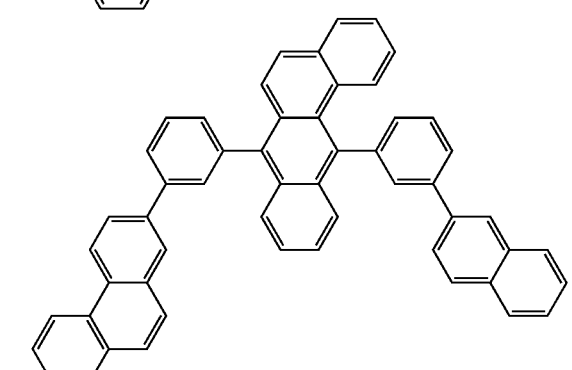
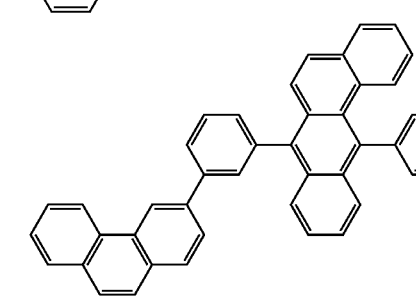
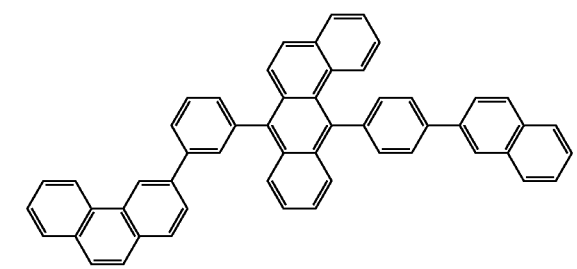

-continued
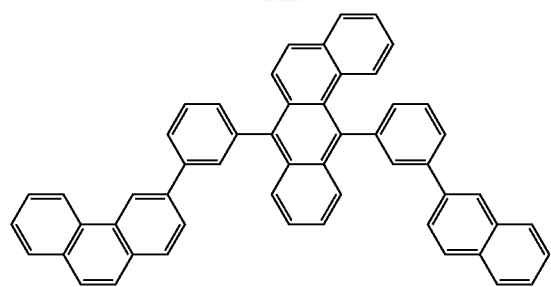
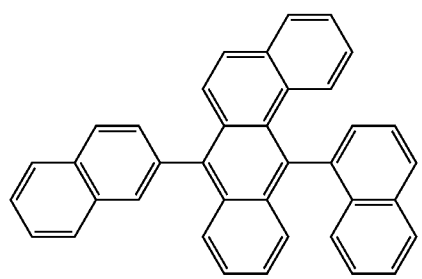
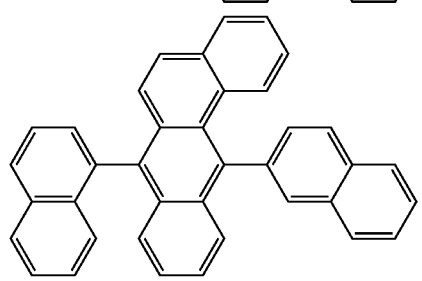
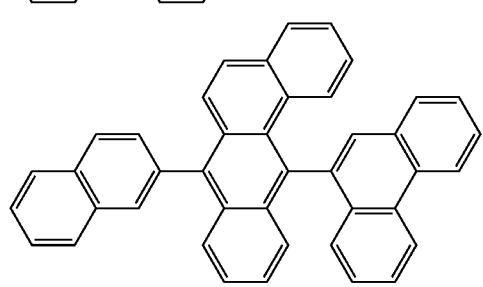
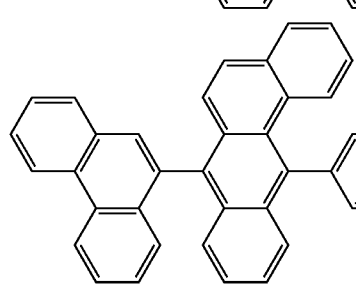
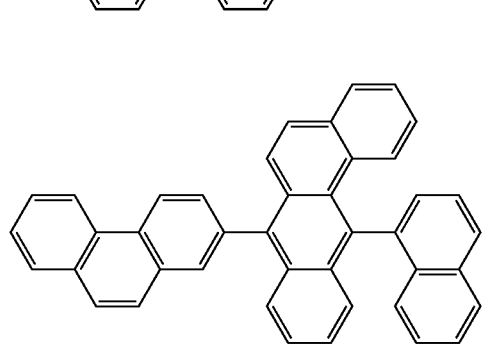
-continued
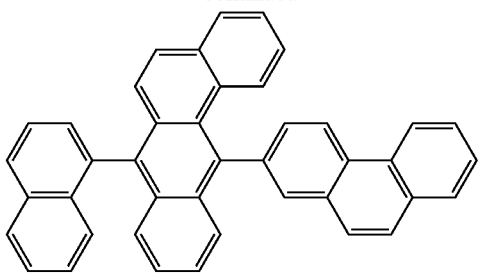
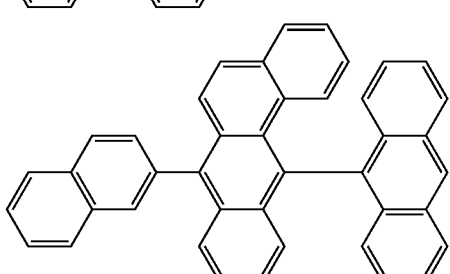
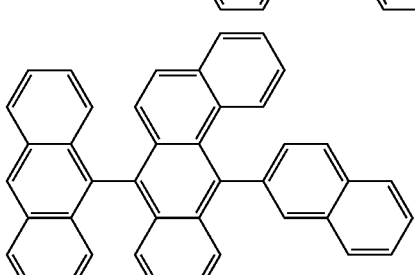
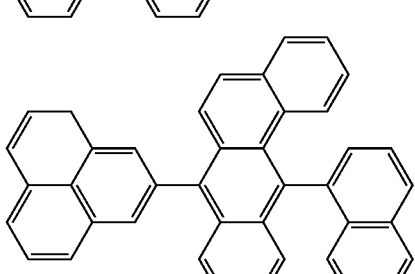
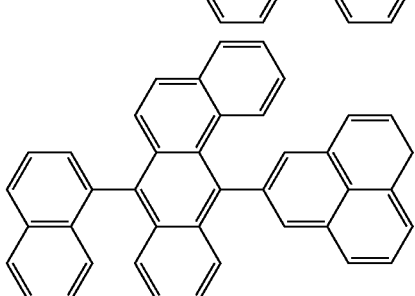
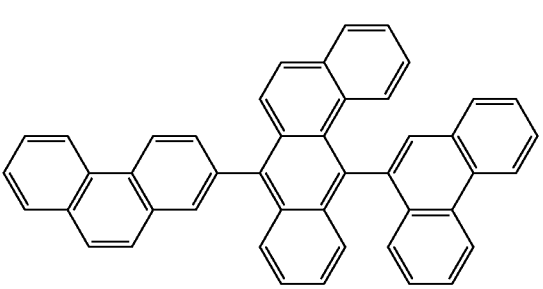

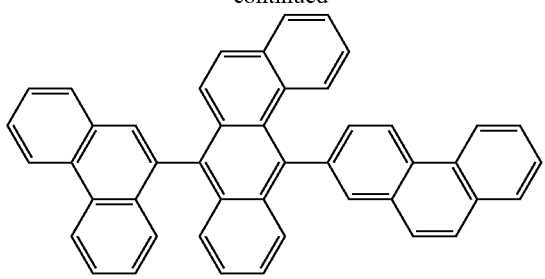

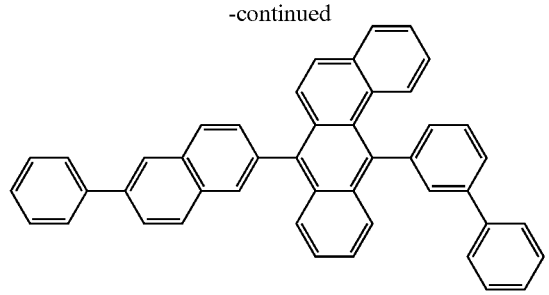
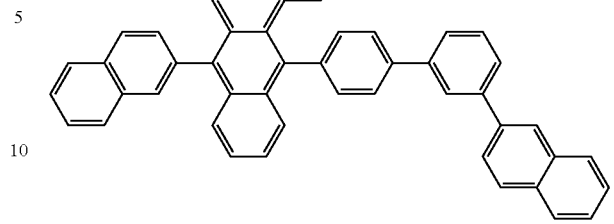
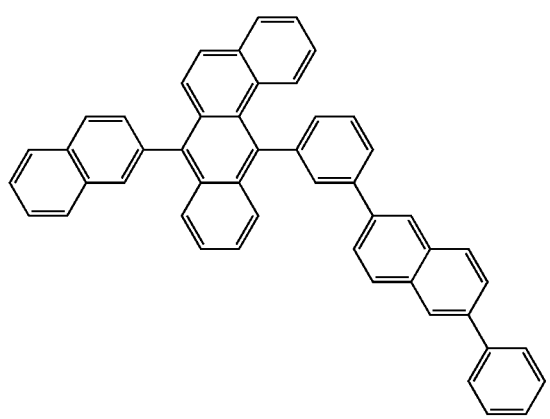
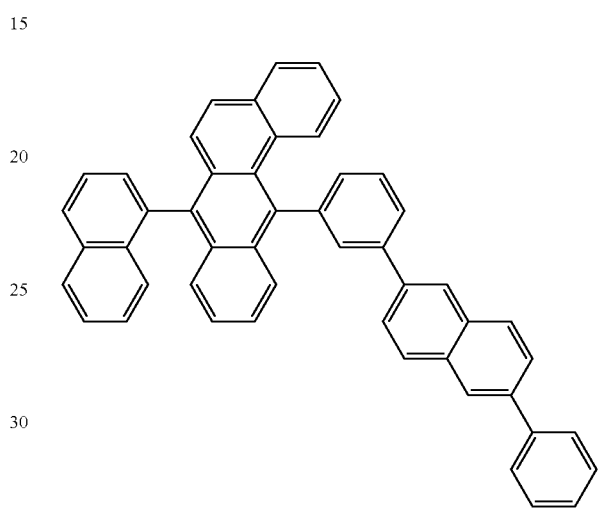
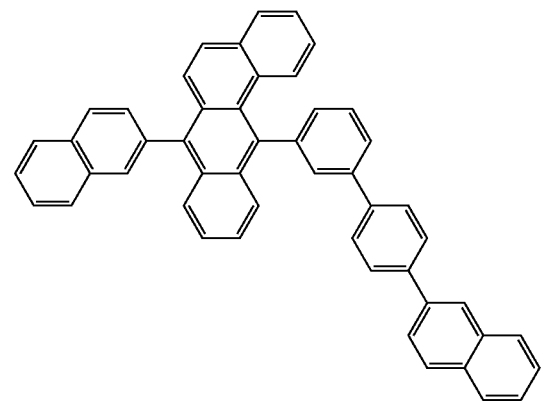
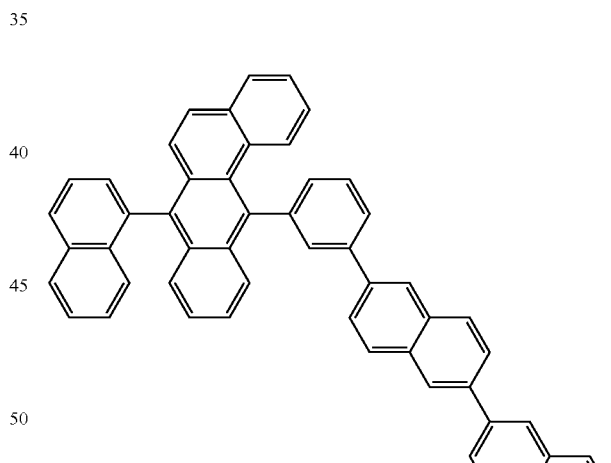
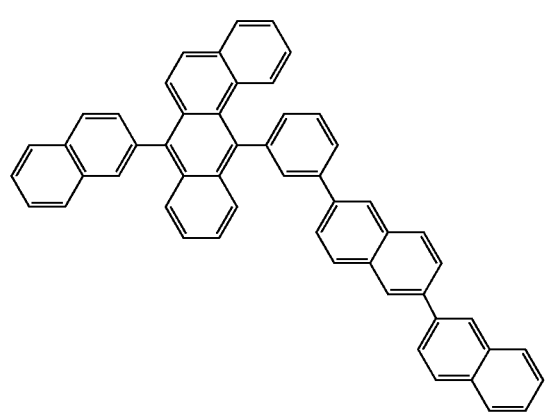
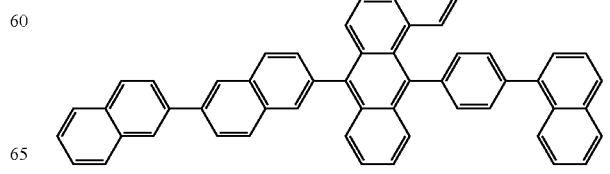

-continued

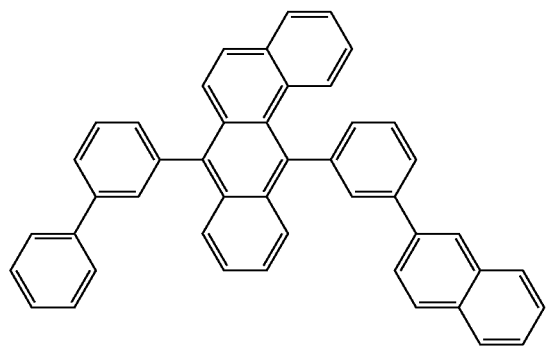
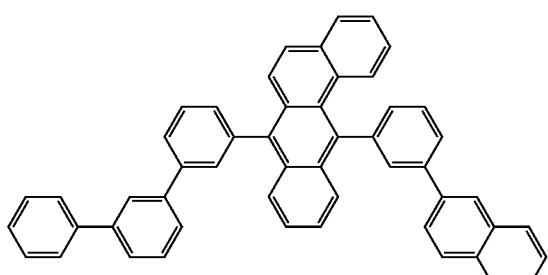
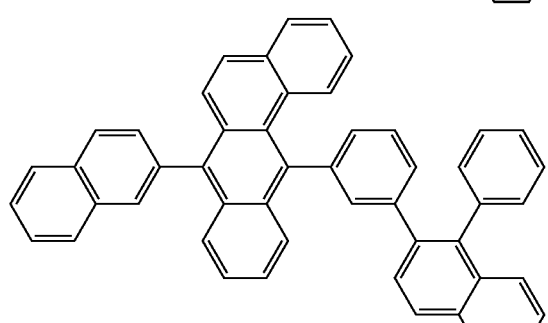
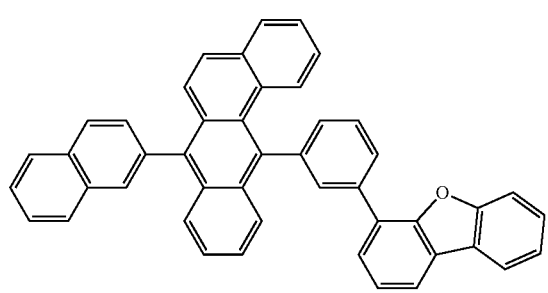
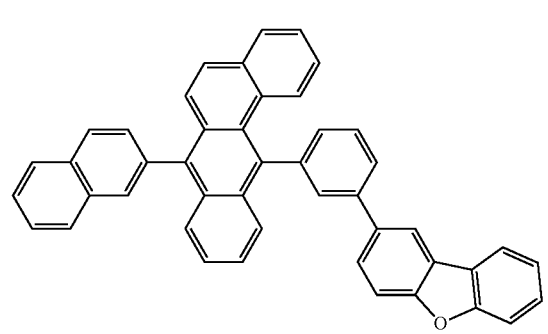

-continued

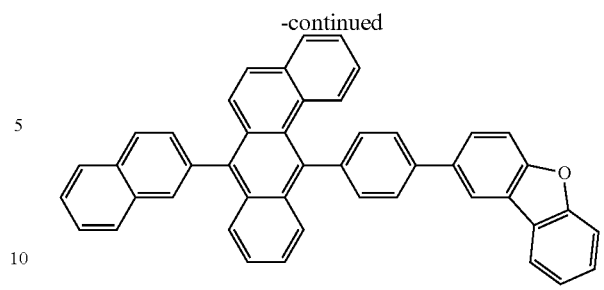
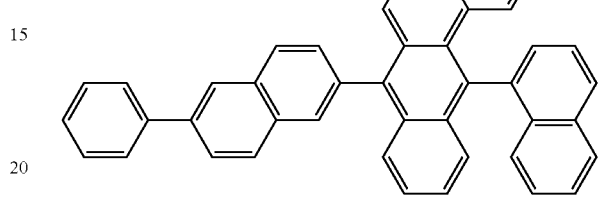
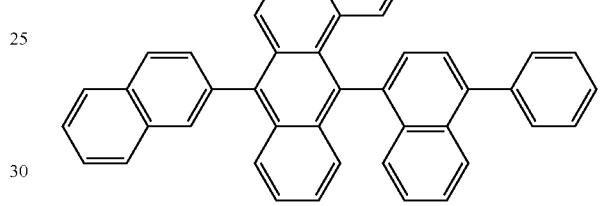
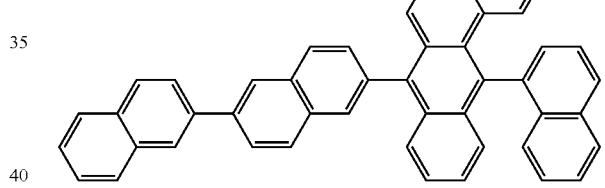
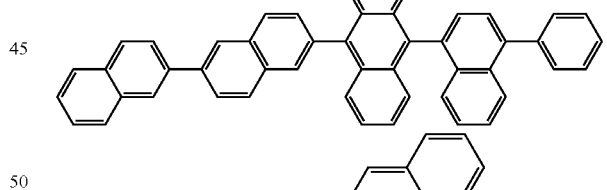
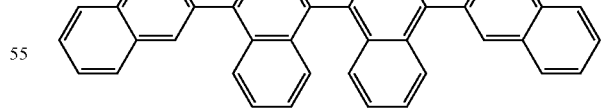

wherein Me is methyl, and TMS is trimethylsilyl.

The benzanthracene compound can be used as an emitting material for an organic EL device.

The organic EL device of the invention comprises an anode, a cathode and one or more organic thin layers comprising an emitting layer between the anode and the cathode, and at least one of the organic thin layers comprise the above-mentioned compound.

A layer containing the above-mentioned compound may contain at least one of a phosphorescent dopant and a fluorescent dopant. The layer can function as a phosphorescent emitting layer and fluorescent emitting layer by containing such dopants.

Representative configurations of the organic EL device of the invention can be given below.
(1) Anode/emitting layer/cathode
(2) Anode/hole-injecting layer/emitting layer/cathode
(3) Anode/emitting layer/electron-injecting layer/cathode
(4) Anode/hole-injecting layer/emitting layer/electron-injecting layer/cathode
(5) Anode/organic semiconductor layer/emitting layer/cathode
(6) Anode/organic semiconductor layer/electron-barrier layer/emitting layer/cathode
(7) Anode/organic semiconductor layer/emitting layer/adhesion-improving layer/cathode
(8) Anode/hole-injecting layer/hole-transporting layer/emitting layer/electron-injecting layer/cathode
(9) Anode/insulating layer/emitting layer/insulating layer/cathode
(10) Anode/inorganic semiconductor layer/insulating layer/emitting layer/insulating layer/cathode
(11) Anode/organic semiconductor layer/insulating layer/emitting layer/insulating layer/cathode
(12) Anode/insulating layer/hole-injecting layer/hole-transporting layer/emitting layer/insulating layer/cathode
(13) Anode/insulating layer/hole-injecting layer/hole-transporting layer/emitting layer/electron-injecting layer/cathode The representative examples of the configuration of the organic EL device of the invention are, however, not limited to the above. Of these, the configuration (8) is preferable.

In the organic EL device of the invention, although the compound of the invention may be used in any of the above-mentioned organic layers, the compound is preferably contained in an emitting region, particularly preferably an emitting layer. The content of the compound is preferably 30 to 100 wt %.

The configuration (8) is shown in FIG. 1. This organic EL device comprises a cathode 10, an anode 20, and a hole-injecting layer 30, a hole-transporting layer 32, an emitting layer 34 and an electron-injecting layer 36 between the anode and the cathode. The hole-injecting layer 30, the hole-transporting layer 32, the emitting layer 34 and the electron-injecting layer 36 correspond to the plurality of organic thin film layers. At least one of these organic thin film layers 30, 32, 34 and 36 comprises the benzanthracene compound.

Each member of the organic EL device will be explained below.

The organic EL device is normally formed on a substrate. The substrate supports the organic EL device. It is preferable to use a smooth substrate. If light is outcoupled through the substrate, it is preferred that the substrate be a transparent substrate with a transmission to visible rays with a wavelength of 400 to 700 nm of 50% or more.

As such transparent substrate, a glass plate, a synthetic resin plate or the like are preferably used. Examples of the glass plate include plates of soda-lime glass, barium/strontium-containing glass, lead glass, aluminosilicate glass, borosilicate glass, barium borosilicate glass, quartz, or the like. Examples of the synthetic resin plates include plates of a polycarbonate resin, an acrylic resin, a polyethylene terephthalate resin, a polyether sulfone resin, a polysulfone resin, or the like.

It is effective that the anode injects holes to the hole-injecting layer, the hole-transporting layer or the emitting layer and has a work function of 4.5 eV or more. Specific examples of the anode material include indium tin oxide (ITO), a mixture of indium oxide and zinc oxide, a mixture of ITO and cerium oxide (ITCO), a mixture of a mixture of indium oxide and zinc oxide, and cerium oxide (IZCO), a mixture of indium oxide and cerium oxide (ICO), a mixture of zinc oxide and aluminum oxide (AZO), tin oxide (NESA), gold, silver, platinum and copper.

The anode can be formed from these electrode materials by a vapor deposition method, a sputtering method or the like.

In the case where emission from the emitting layer is outcoupled through the anode, the transmittance of the anode to the emission is preferably more than 10%. The sheet resistance of the anode is preferably several hundred $\Omega/\square$ or less. The film thickness of the anode, which varies depending upon the material thereof, is usually from 10 nm to 1 μm, preferably from 10 to 200 nm.

The emitting layer has the following functions.
(i) Injection function: function of allowing injection of holes from the anode or hole-injecting layer and injection of electrons from the cathode or electron-injecting layer upon application of an electric field
(ii) Transporting function: function of moving injected carriers (electrons and holes) due to the force of an electric field
(iii) Emission function: function of recombining electons and holes to emit light As the method of forming the emitting layer, a known method such as deposition, spin coating, or an LB method may be applied. It is preferable that the emitting layer be a molecular deposition film. The molecular deposition film is a film formed by deposition of a material compound in a gas phase, or by solidification of a material compound in the form of a solution or in a liquid phase. The molecular deposition film can be usually distinguished from a thin film (molecular accumulation film) formed using the LB method by the difference in aggregation structure or higher order structure or the difference in function due to the difference in structure.

The emitting layer may also be formed by dissolving a binder such as a resin and a material compound in a solvent to obtain a solution, and forming a thin film from the solution by spin coating or the like.

Examples of the emission material or the dopant material which can be used in the emitting layer include anthracene, naphthalene, phenanthrene, pyrene, tetracene, coronene, chrysene, fluoresceine, perylene, phthaloperylene, naphthaloperylene, perynone, phthaloperynone, naphthaloperynone, diphenylbutadiene, tetraphenylbutadiene, coumarin, oxadizole, aldazine, bisbenzoxazoline, bisstyryl, pyrazine, cyclopentadiene, quinoline metal complex, aminoquinoline metal complex, benzoquinoline metal complex, imine, diphenylethylene, vinylanthracene, diaminocarbazole, pyrane, thiopyran, polymethine, merocyanine, imidazole chelated oxynoid compound, quinacridon, rubrene, derivatives thereof, and fluorescent dyes, but they are not limited thereto.

Specific examples of the host material which can be used in the emitting layer include compounds shown by the following formulas (i) to (ix):

Asymmetrical Anthracene Represented by the Following Formula (i):

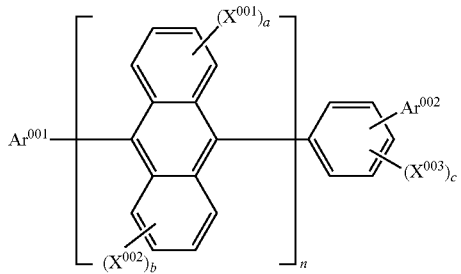

wherein $Ar^{001}$ is a substituted or unsubstituted fused aromatic group having 10 to 50 ring carbon atoms, $Ar^{002}$ is a substituted or unsubstituted aromatic group having 6 to 50 ring carbon atoms, $X^{001}$ to $X^{003}$ are independently a substituted or unsubstituted aromatic group having 6 to 50 ring carbon atoms, a substituted or unsubstituted aromatic heterocyclic group having 5 to 50 atoms that form a ring (hereinafter referred to as "ring atoms"), a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a carboxyl group, a halogen atom, a cyano group, a nitro group and a hydroxy group, a, b and c are each an integer of 0 to 4.

n is an integer of 1 to 3, and when n is two or more, groups in the [ ] may be the same or different.

Asymmetrical Monoanthracene Derivatives Represented by the Following Formula (ii):

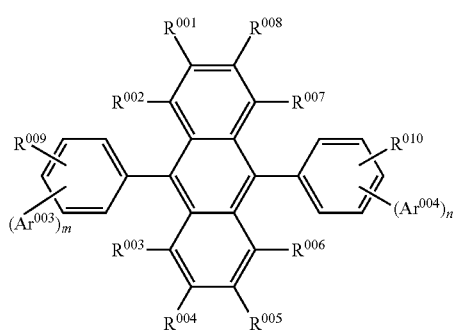

wherein $Ar^{003}$ and $Ar^{004}$ are independently are a substituted or unsubstituted aromatic ring group having 6 to 50 ring carbon atoms, m and n are each an integer of 1 to 4, provided that in the case where m=n=1 and $Ar^{003}$ and $Ar^{004}$ are symmetrically bonded to the benzene rings, $Ar^{003}$ and $Ar^{004}$ are not the same, and in the case where m or n is an integer of 2 to 4, m is different from n, $R^{001}$ to $R^{010}$ are independently are a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group.

Asymmetrical Pyrene Derivatives Shown by the Following Formula (iii):

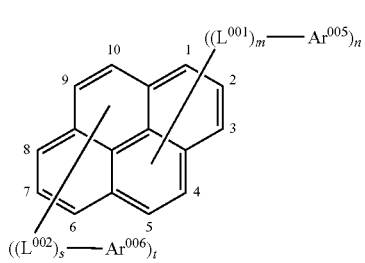

wherein $Ar^{005}$ and $Ar^{006}$ are independently an aromatic group having 6 to 50 ring carbon atoms, $L^{001}$ and $L^{002}$ are independently a substituted or unsubstituted phenylene group, a substituted or unsubstituted naphthalenylene group, a substituted or unsubstituted fluolenylene group, or a substituted or unsubstituted dibenzosilolylene group, m is an integer of 0 to 2, n is an integer of 1 to 4, s is an integer of 0 to 2, and t is an integer of 0 to 4, $L^{001}$ or $Ar^{005}$ bonds at any one position of 1 to 5 of the pyrene, and $L^{002}$ or $Ar^{006}$ bonds at any one position of 6 to 10 of the pyrene; provided that when n+t is an even number, $Ar^{005}$, $Ar^{006}$, $L^{001}$ and $L^{002}$ satisfy the following (1) and (2):

(1) $Ar^{005} \neq Ar^{006}$ and/or $L^{001} \neq L^{002}$ where $\neq$ means these substituents are groups having different structures from each other, (2) when $Ar^{005} = Ar^{006}$ and $L^{001} = L^{002}$, (2-1) m≠s and/or n≠t, or (2-2) when m=s and n=t, (2-2-1) when $L^{001}$ and $L^{002}$ or pyrene are independently bonded to different bonding positions of $Ar^{005}$ and $Ar^{006}$, or (2-2-2) when $L^{001}$ and $L^{002}$ or pyrene are bonded to the same position of $Ar^{005}$ and $Ar^{006}$, the positions of the substitution of $L^{001}$ and $L^{002}$ or $Ar^{005}$ and $Ar^{006}$ at pyrene are neither the 1$^{st}$ position and the 6$^{th}$ position, nor the 2$^{nd}$ position and the 7$^{th}$ position.

Asymmetrical Anthracene Shown by the Following Formula (iv):

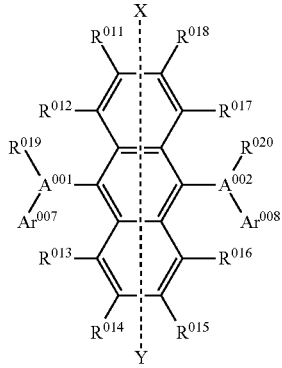

(iv)

wherein $A^{001}$ and $A^{002}$ are independently a substituted or unsubstituted fused aromatic ring group having 10 to 20 ring carbon atoms, $Ar^{007}$ and $Ar^{006}$ are independently a hydrogen atom or a substituted or unsubstituted aromatic ring group having 6 to 50 ring carbon atoms, $R^{011}$ to $R^{020}$ are independently are a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group, and there may be a plurality of $Ar^{007}$, $Ar^{008}$, $R^{019}$ and $R^{020}$, respectively, and adjacent groups thereof may form a saturated or unsaturated ring structure, provided that groups do not symmetrically bond to 9 and 10 positions of the central anthracene with respect to X-Y axis.

Anthracene Derivative Represented by the Following Formula (v):

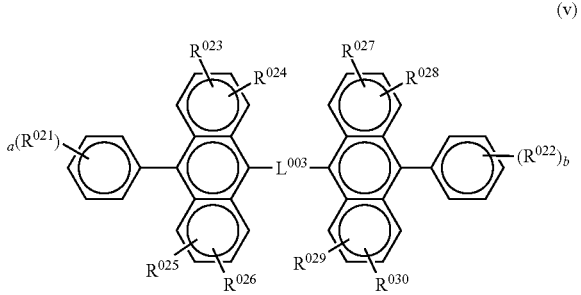

(v)

wherein $R^{021}$ to $R^{030}$ are independently a hydrogen atom, an alkyl group, a cycloalkyl group, a substituted or unsubstituted aryl group, an alkoxy group, an aryloxy group, an alkylamino group, an alkenyl group, an arylamino group or a substituted or unsubstituted heterocyclic group, a and b are independently an integer of 1 to 5, and when they are two or more, $R^{021}$s or $R^{022}$s may be the same or different, $R^{021}$s or $R^{022}$s may be bonded to form a ring, $R^{023}$ and $R^{024}$, $R^{025}$ and $R^{026}$, $R^{027}$ and $R^{028}$, and $R^{029}$ and $R^{030}$ may be bonded to each other to form a ring, and $L^{003}$ is a single bond, —O—, —S—, —N(R)— (R is an alkyl group or a substituted or unsubstituted aryl group), an alkylene group or an arylene group.

Anthracene Derivative Shown by the Following Formula (vi):

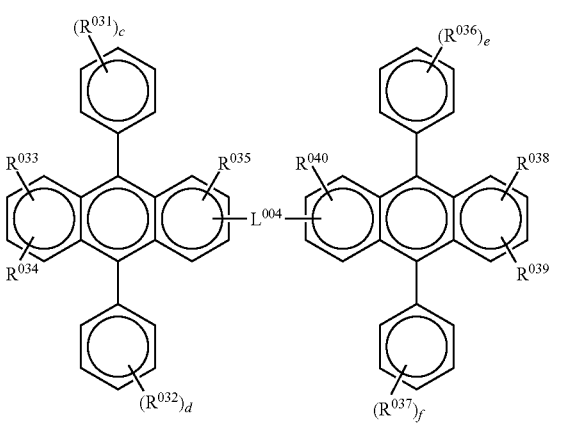

(vi)

wherein $R^{031}$ to $R^{040}$ are independently a hydrogen atom, an alkyl group, a cycloalkyl group, an aryl group, an alkoxy group, an aryloxy group, an alkylamino group, an arylamino group or a substituted or unsubstituted heterocyclic group, c, d, e and f are independently an integer of 1 to 5, and when they are two or more, $R^{031}$s, $R^{032}$s, $R^{036}$s or $R^{037}$s may be the same or different, $R^{031}$s, $R^{032}$s, $R^{033}$s or $R^{037}$s may be bonded to form a ring, and $R^{033}$ and $R^{034}$, and $R^{039}$ and $R^{040}$ may be bonded to each other to form a ring, and $L^{004}$ is a single bond, —O—, —S—, —N(R)— (R is an alkyl group or a substituted or unsubstituted aryl group), an alkylene group or an arylene group.

Spirofluorene Derivative Represented by the Following Formula (vii):

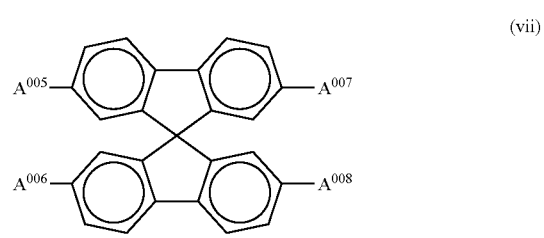

(vii)

wherein $A^{005}$ to $A^{008}$ are independently a substituted or unsubstituted biphenyl or a substituted or unsubstituted naphthyl group.

Fused Ring-containing Compounds Shown by the Following Formula (viii):

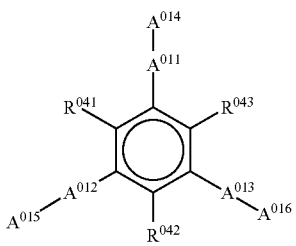

wherein $A^{011}$ to $A^{013}$ are independently a substituted or unsubstituted arylene group having 6 to 50 ring carbon atoms,
$A^{014}$ to $A^{016}$ are independently a hydrogen atom or a substituted or unsubstituted aryl group having 6 to 50 ring carbon atoms, and
$R^{041}$ to $R^{043}$ are independently a hydrogen atom, alkyl group having 1 to 6 carbon atoms, cycloalkyl group having 3 to 6 carbon atoms, alkoxy group having 1 to 6 carbon atoms, aryloxy group having 5 to 18 carbon atoms, aralkyloxy group having 7 to 18 carbon atoms, arylamino group having 5 to 16 carbon atoms, nitro group, cyano group, ester group having 1 to 6 carbon atoms, or a halogen atom, provided that at least one of $A^{011}$ to $A^{016}$ is a group having a fused aromatic ring with three or more rings.

Fluorene Compounds Shown by the Following Formula (ix):

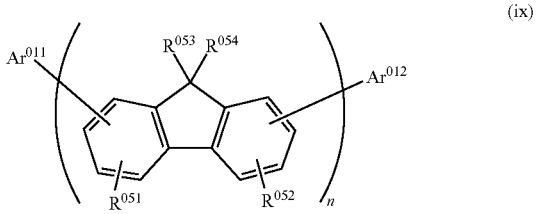

wherein $R^{051}$ and $R^{052}$ are a hydrogen atom, a substituted or unsubstituted alkyl group, a substituted or unsubstituted aralkyl group, a substituted or unsubstituted aryl group, a substituted or unsubstituted heterocyclic group, substituted amino group, cyano group, or a halogen atom,
$R^{051}$s or $R^{052}$s bonded to different fluorene groups may be the same or different, and $R^{051}$ and $R^{052}$ bonded to a single fluorene group may be the same or different,
$R^{053}$ and $R^{054}$ are independently a hydrogen atom, a substituted or unsubstituted alkyl group, a substituted or unsubstituted aralkyl group, a substituted or unsubstituted aryl group or a substituted or unsubstituted heterocyclic group, $R^{053}$s or $R^{054}$s bonded to different fluorene groups may be the same or different, and $R^{053}$ and $R^{054}$ bonded to a single fluorene group may be the same or different,
$Ar^{011}$ and $Ar^{012}$ are a substituted or unsubstituted fused polycyclic aromatic group with a total number of benzene rings of three or more or a fused polycyclic heterocyclic group which is bonded to the fluorene group through substituted or unsubstituted carbon and has a total number of benzene rings and heterocyclic rings of three or more, provided that $Ar^{011}$ and $Ar^{012}$ may be the same or different and n is an integer of 1 to 10.

In the organic EL device of the invention, the emitting layer may contain a phosphorescent dopant and/or a fluorescent dopant in addition to the emitting material of the present invention. An emitting layer containing these dopants may be stacked on an emitting layer containing the compound of the invention.

A phosphorescent dopant is a compound that can emit light from triplet excitons. The dopant is not limited so long as it can emit light from triplet excitons, but it is preferably a metal complex containing at least one metal selected from the group of Ir, Ru, Pd, Pt, Os and Re. A porphyrin metal complex or an ortho-metalated metal complex is preferable. The phosphorescent compounds can be used individually or as a combination of two or more kinds.

As a porphyrin metal complex, a porphyrin platinum complex is preferable.

There are various ligands forming an ortho-metalated metal complex. Preferable ligands include compounds having a phenylpyridine skeleton, a bipyridyl skeleton or a phenanthroline skeleton, 2-phenylpyridine, 7,8-benzoquinoline, 2-(2-thienyl)pyridine, 2-(1-naphthyl)pyridine and 2-phenylquinoline derivatives. These ligands may have a substituent, if necessary. Ligands to which fluorides, e.g. a trifluoromethyl group, being introduced as a substituent are particularly preferable as a blue dopant. As an auxiliary ligand, preferred are ligands other than the above-mentioned ligands, such as acetylacetonate and picric acid may be contained.

Specific examples of such metal complex are, not limited to, tris(2-phenylpyridine)iridium, tris(2-phenylpyridine)ruthenium, tris(2-phenylpyridine)palladium, bis(2-phenylpyridine)platinum, tris(2-phenylpyridine)osmium, tris(2-phenylpyridine)rhenium, octaethylplatinumporphyrin, octaphenylplatinumporphyrin, octaethylpalladiumporphyrin, octaphenylpalladiumporphyrin and the like. A suitable complex is selected according to a required light color, device performance and host material used.

The content of a phosphorescent dopant in an emitting layer is not limited and can be properly selected according to purposes; for example, it is 0.1 to 70 mass %, preferably 1 to 30 mass %. When the content of a phosphorescent compound is less than 0.1 mass %, emission may be weak and the advantages thereof may not be sufficiently obtained. When the content exceeds 70 mass %, the phenomenon called concentration quenching may significantly proceed, thereby degrading the device performance.

As for the fluorescent dopant, it is preferable to select a compound from amine-based compounds, aromatic compounds, chelate complexes such as tris(8-quinolilate)aluminum complexes, coumarin derivatives, tetraphenylbutadiene derivatives, bisstyrylarylene derivatives, oxadiazole derivatives or the like, taking into consideration required emission colors. Of these, styrylamine compounds, styryldiamine compounds, arylamine compounds and aryldiamine compounds are further preferable. Fused polycyclic aromatic compounds which are not an amine compound are also preferable. These fluorescent dopants may be used singly or in combination of two or more.

As the styrylamine compound and the styryldiamine compound, those shown by the following formula (A) are preferable.

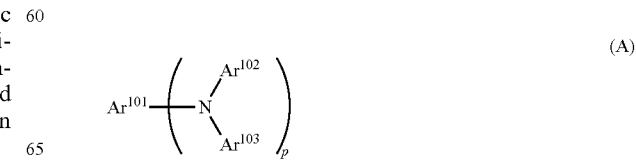

wherein Ar¹⁰¹ is a group with a valence of p corresponding to a phenyl group, a naphthyl group, a biphenyl group, a terphenyl group, a stilbenzyl group or a distyrylaryl group, Ar¹⁰² and Ar¹⁰³ are independently an aromatic hydrocarbon group having 6 to 20 carbon atoms, Ar¹⁰¹, Ar¹⁰² and Ar¹⁰³ may be substituted, one of Ar¹⁰¹ to Ar¹⁰³ is substituted by a styryl group, further preferably, at least one of Ar¹⁰² and Ar¹⁰³ is substituted by a styryl group, and p is an integer of 1 to 4, preferably an integer of 1 to 2.

Here, as the aromatic hydrocarbon group having 6 to 20 carbon atoms, a phenyl group, a naphthyl group, an anthranyl group, a phenanthryl group, a terphenyl group or the like can be given.

As the arylamine compound and the aryldiamine compound, those shown by the following formula (B) are preferable.

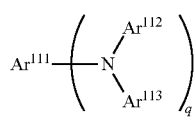

(B)

wherein A¹¹¹ is a substituted or unsubstituted aromatic group with a valence of q having 5 to 40 ring carbon atoms, Ar¹¹² and Ar¹¹³ are independently a substituted or unsubstituted aryl group having 5 to 40 ring carbon atoms, and q is an integer of 1 to 4, preferably an integer of 1 to 2.

Examples of the aryl group having 5 to 40 ring carbon atoms include a phenyl group, a naphthyl group, an anthranyl group, a phenanthryl group, a pyrenyl group, a coronenyl group, a biphenyl group, a terphenyl group, a pyrrolyl group, a furyl group, a thienyl group, a benzothienyl group, an oxadiazolyl group, a diphenylanthranyl group, an indolyl group, a carbazolyl group, a pyridyl group, a benzoquinolyl group, a fluoranthenyl group, an acenaphthofluoranthenyl group, a stilbene group, a perylenyl group, a chrysenyl group, a picenyl group, a triphenylenyl group, a rubicenyl group, a benzanthracenyl group, a phenylanthranyl group and a bisanthracenyl group. Preferred are a naphthyl group, an anthranyl group, chrysenyl group and a pyrenyl group.

Preferred substituents for the above-mentioned aryl group include an alkyl group having 1 to 6 carbon atoms (ethyl, methyl, i-propyl, n-propyl, s-butyl, t-butyl, pentyl, hexyl, cyclopentyl, cyclohexyl, or the like); an alkoxy group having 1 to 6 carbon atoms (ethoxy, methoxy, i-propoxy, n-propoxy, s-buthoxy, t-buthoxy, penthoxy, hexyloxy, cyclopentoxy, cyclohexyloxy, or the like); an aryl group having 5 to 40 ring carbon atoms; an amino group substituted with an aryl group having 5 to 40 ring carbon atoms; an ester group with an aryl group having 5 to 40 ring carbon atoms; an ester group with an alkyl group having 1 to 6 carbon atoms; a cyano group; a nitro group; and a halogen atom.

The emitting layer may contain hole-transporting materials, electron-transporting materials and polymer binders, if necessary.

The thickness of an emitting layer is preferably from 5 to 50 nm, more preferably from 7 to 50 nm and most preferably from 10 to 50 nm. When it is less than 5 nm, the formation of an emitting layer and the adjustment of chromaticity may become difficult. When it exceeds 50 nm, the driving voltage may increase.

The hole-transporting layer and the hole-injecting layer are layers which help the injection of holes into the emitting layer so as to transport holes to an emitting region, and have a large hole mobility and normally have such a small ionization energy as 5.5 eV or less. As the material for the hole-injecting layer and the hole-transporting layer, a material which transports holes to the emitting layer at a lower electrical field is preferable, and the hole mobility thereof is preferably 10⁻⁴ cm²/V·second or more when an electric field of, e.g., 10⁴ to 10⁶ V/cm is applied.

There are no particular restrictions on the material for the hole-injecting layer and the hole-transporting layer. The material can be arbitrarily selected from materials which have been widely used as a hole-transporting material of photo-conductive materials and known materials used in a hole-injecting layer and a hole-transporting layer of organic EL devices.

In the hole-injecting layer and the hole-transporting layer, an aromatic amine derivative shown by the following formula can be used, for example.

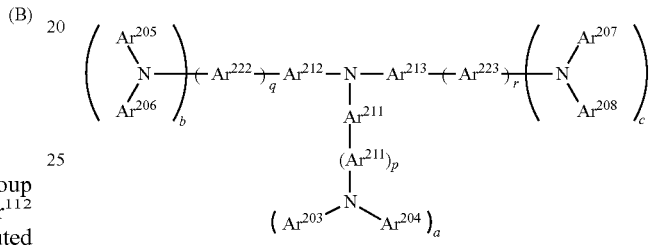

wherein Ar²¹¹ to Ar²¹³, Ar²²¹ to Ar²²³ and Ar²⁰³ to Ar²⁰⁸ are independently a substituted or unsubstituted aromatic hydrocarbon group having 6 to 50 ring carbon atoms or a substituted or unsubstituted aromatic heterocyclic group having 5 to 50 ring atoms, a to c and p to r are independently an integer of 0 to 3, and Ar²⁰³ and Ar²⁰⁴, Ar²⁰⁵ and Ar²⁰⁶, or Ar²⁰⁷ and Ar²⁰⁸ may be bonded to each other to form a saturated or unsaturated ring.

Specific examples of the substituted or unsubstituted aromatic hydrocarbon groups having 6 to 50 ring carbon atoms include a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, and 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4"-t-butyl-p-terphenyl-4-yl group.

Specific examples of the substituted or unsubstituted aromatic heterocyclic group having 5 to 50 ring atoms include a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indoryl group, a 2-indoryl group, a 3-indoryl group, a 4-indoryl group, a 5-indolyl group, a 6-indolyl group, a 7-indolyl group, a 1-isoindoryl group, a 2-isoindoryl group, a 3-isoindolyl group, a 4-isoindolyl group, a 5-isoindolyl group, a 6-isoindolyl group, a 7-isoindolyl group, a 2-furyl group, a 3-furyl group, a 2-benzofuryl group, a 3-benzofuryl group, a 4-benzofuryl group, a 5-benzofuryl group, a 6-benzofuryl group, a 7-benzofuryl group, a 1-isobenzofuryl group, a 3-isobenzofuryl group, a 4-isobenzofuryl group, a 5-isobenzofuryl group, a 6-isobenzofuryl group, a 7-isobenzofuryl group, a quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthrolin-2-yl group, a 1,7-phenanthrolin-3-yl group, a 1,7-phenanthrolin-4-yl group, a 1,7-phenanthrolin-5-yl group, a 1,7-phenanthrolin-6-yl group, a 1,7-phenanthrolin-8-yl group, a 1,7-phenanthrolin-9-yl group, a 1,7-phenanthrolin-10-yl group, a 1,8-phenanthrolin-2-yl group, a 1,8-phenanthrolin-3-yl group, a 1,8-phenanthrolin-4-yl group, a 1,8-phenanthrolin-5-yl group, a 1,8-phenanthrolin-6-yl group, a 1,8-phenanthrolin-7-yl group, a 1,8-phenanthrolin-9-yl group, a 1,8-phenanthrolin-10-yl group, a 1,9-phenanthrolin-2-yl group, a 1,9-phenanthrolin-3-yl group, a 1,9-phenanthrolin-4-yl group, a 1,9-phenanthrolin-5-yl group, a 1,9-phenanthrolin-6-yl group, a 1,9-phenanthrolin-7-yl group, a 1,9-phenanthrolin-8-yl group, a 1,9-phenanthrolin-10-yl group, a 1,10-phenanthrolin-2-yl group, a 1,10-phenanthrolin-3-yl group, a 1,10-phenanthrolin-4-yl group, a 1,10-phenanthrolin-5-yl group, a 2,9-phenanthrolin-1-yl group, a 2,9-phenanthrolin-3-yl group, a 2,9-phenanthrolin-4-yl group, a 2,9-phenanthrolin-5-yl group, a 2,9-phenanthrolin-6-yl group, a 2,9-phenanthrolin-7-yl group, a 2,9-phenanthrolin-8-yl group, a 2,9-phenanthrolin-10-yl group, a 2,8-phenanthrolin-1-yl group, a 2,8-phenanthrolin-3-yl group, a 2,8-phenanthrolin-4-yl group, a 2,8-phenanthrolin-5-yl group, a 2,8-phenanthrolin-6-yl group, a 2,8-phenanthrolin-7-yl group, a 2,8-phenanthrolin-9-yl group, a 2,8-phenanthrolin-10-yl group, a 2,7-phenanthrolin-1-yl group, a 2,7-phenanthrolin-3-yl group, a 2,7-phenanthrolin-4-yl group, a 2,7-phenanthrolin-5-yl group, a 2,7-phenanthrolin-6-yl group, a 2,7-phenanthrolin-8-yl group, a 2,7-phenanthrolin-9-yl group, a 2,7-phenanthrolin-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrol-1-yl group, a 2-methylpyrrol-3-yl group, a 2-methylpyrrol-4-yl group, a 2-methylpyrrol-5-yl group, a 3-methylpyrrol-1-yl group, a 3-methylpyrrol-2-yl group, a 3-methylpyrrol-4-yl group, a 3-methylpyrrol-5-yl group, a 2-t-butylpyrrol-4-yl group, a 3-(2-phenylpropyl)pyrrol-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group and a 4-t-butyl-3-indolyl group.

Further, the compound shown by the following formula can be used in the hole-injecting layer and the hole-transporting layer.

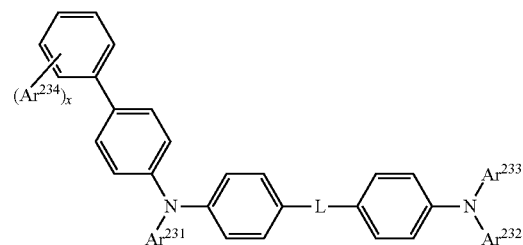

wherein $Ar^{231}$ to $Ar^{234}$ are independently a substituted or unsubstituted aromatic hydrocarbon group having 6 to 50 ring carbon atoms, or a substituted or unsubstituted aromatic heterocyclic group having 5 to 50 ring atoms, L is a linking group, which is a single bond, a substituted or unsubstituted aromatic hydrocarbon group having 6 to 50 ring carbon atoms or a substituted or unsubstituted aromatic heterocyclic group having 5 to 50 ring atoms, x is an integer of 0 to 5, and $Ar^{232}$ and $Ar^{233}$ may be bonded to each other to form a saturated or unsaturated ring.

As specific examples of the substituted or unsubstituted aromatic hydrocarbon group having 6 to 50 ring carbon atoms and substituted or unsubstituted aromatic heterocyclic group having 5 to 50 ring atoms, the same as those exemplified above can be given.

As specific examples of the material for the hole-injecting layer and the hole-transporting layer, a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalkone derivative, an oxazole derivative, a styrylanthracene derivative, a fluorenone derivative, a hydrazone derivative, a stilbene derivative, a silazane derivative, an aniline-based copolymer, and conductive high-molecular oligomers (in particular, a thiophene oligomer) can be given.

As the material for the hole-injecting layer and the hole-transporting layer, although the above-mentioned materials can be used, it is preferable to use a porphyrin compound, an aromatic tertiary amine compound and a styrylamine compound. It is particularly preferable to use an aromatic tertiary amine compound.

It is preferable to use a compound having two fused aromatic rings in the molecule thereof, for example, 4,4'-bis(N-(1-naphthyl)-N-phenylamino)biphenyl (abbreviated by NPD, hereinafter), and 4,4',4''-tris(N-(3-methylphenyl)-N-phenylamino)triphenylamine (abbreviated by MTDATA, hereinafter) wherein three triphenylamine units are linked in a star-burst form.

In addition to the above, a nitrogen-containing heterocyclic derivative shown by the following formula can also be used.

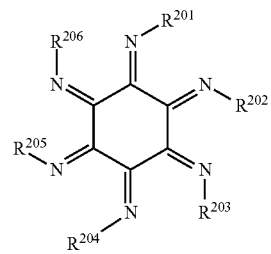

wherein $R^{201}$ to $R^{206}$ are independently a substituted or unsubstituted alkyl group, a substituted or unsubstituted aryl group, a substituted or unsubstituted aralkyl group, a substituted or unsubstituted heterocyclic group, and $R^{201}$ and $R^{202}$, $R^{203}$ and $R^{204}$, $R^{205}$ and $R^{206}$, $R^{201}$ and $R^{206}$, $R^{202}$ and $R^{203}$, or $R^{204}$ and $R^{205}$ may form a fused ring.

Further, the following compound can also be used.

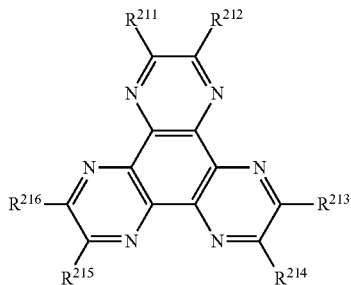

wherein $R^{211}$ to $R^{216}$ are substituents; preferably they are independently an electron-attracting group such as a cyano group, a nitro group, a sulfonyl group, a carbonyl group, a trifluoromethyl group and a halogen.

Further, an inorganic compound such as p-type Si and p-type SiC can also be used as a material for the hole-injecting layer and the hole-transporting layer.

The hole-injecting layer and the hole-transporting layer can be formed from the above-mentioned compounds by a known method such as vapor vacuum deposition, spin coating, casting or LB technique. The film thickness of the hole-injecting layer and the hole-transporting layer is not particularly limited, and is usually from 5 nm to 5 μm. The hole-injecting layer and the hole-transporting layer may be a single layer made of one or two or more of the above-mentioned materials, or may be of a structure in which hole-injecting layers and hole-transporting layers made of different compounds are stacked.

The organic semiconductor layer is a layer for helping the injection of holes or electrons into the emitting layer, and is preferably a layer having an electric conductivity of $10^{-10}$ S/cm or more. As the material of such an organic semiconductor layer, electroconductive oligomers such as thiophene-containing oligomers or arylamine-containing oligomers and electroconductive dendrimers such as arylamine-containing dendrimers may be used.

The electron-injecting layer and the electron-transporting layer are layers which assist injection of electrons into the emitting layer and transport electrons to the emitting region, and exhibit a high electron mobility. The adhesion-improving layer is a kind of the electron-injecting layer which is made of a material exhibiting particularly good adhesion to the cathode.

The thickness of the electron-transporting layer is arbitrarily selected in the range of 5 nm to 5 μm. When the electron-transporting layer has a thick thickness, it is preferable that the electron mobility be $10^{-5}$ cm$^2$/Vs or more at an applied electric field of $10^4$ to $10^6$ V/cm in order to prevent an increase in voltage.

The material used in the electron-injecting layer and the electron-transporting layer is preferably a metal complex of 8-hydroxyquinoline or a derivative thereof, or an oxadiazole derivative. Specific examples of the metal complex of 8-hydroxyquinoline or derivative thereof include metal chelate oxynoid compounds containing a chelate of oxine (generally, 8-quinolinol or 8-hydroxyquinoline), e.g. tris(8-quinolinolato)aluminum.

As examples of the oxadiazole derivative, an electron-transporting compound shown by the following formula can be given.

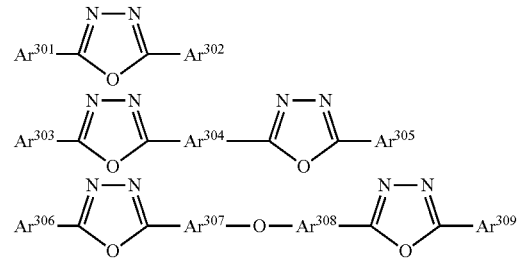

wherein $Ar^{301}$, $Ar^{302}$, $Ar^{303}$, $Ar^{305}$, $Ar^{306}$ and $Ar^{309}$ are independently a substituted or unsubstituted aryl group, and $Ar^{304}$, $Ar^{307}$ and $Ar^{308}$ are independently a substituted or unsubstituted arylene group.

As examples of the aryl group, a phenyl group, a biphenyl group, an anthranyl group, a perylenyl group, and a pyrenyl group can be given. As examples of the arylene group, a phenylene group, a naphthylene group, a biphenylene group, an anthranylene group, a perylenylene group, a pyrenylene group, and the like can be given. As the substituent, an alkyl group having 1 to 10 carbon atoms, an alkoxy group having 1 to 10 carbon atoms, a cyano group, and the like can be given. The electron-transporting compound is preferably one from which a thin film can be formed.

The following compounds can be given as specific examples of the electron-transporting compound.

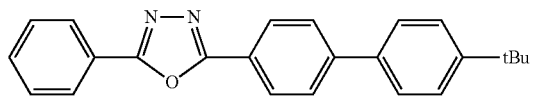

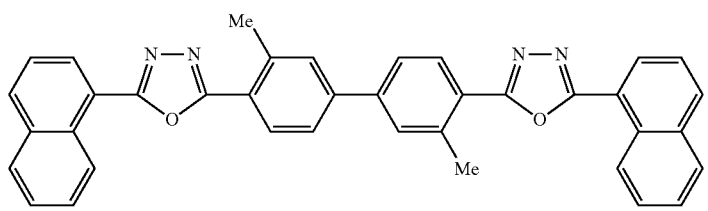

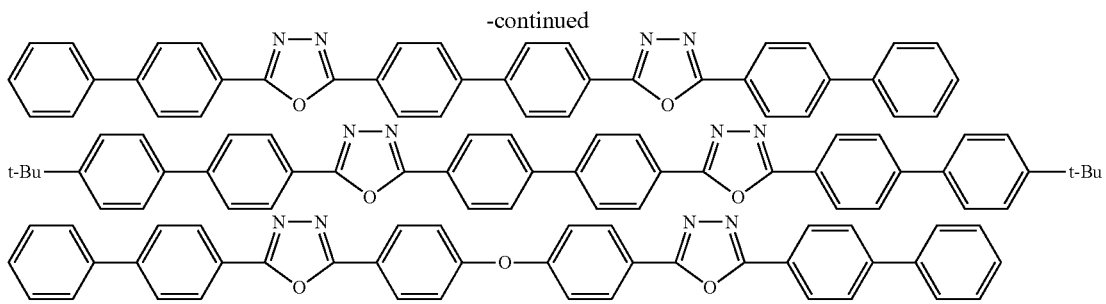

(Me is Methyl and tBu is T-Butyl.)

Furthermore, as materials used for the electron-injecting layer and electron-transporting layer, the compounds represented by the following formulas (E) to (J) may be used.

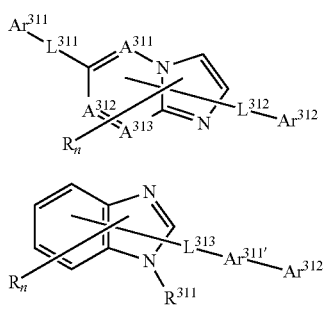

Nitrogen-containing Heterocyclic Derivatives Shown by the Formulas (E) and (F):
wherein $Ar^{311}$ to $Ar^{313}$ are independently a nitrogen atom or a carbon atom, $Ar^{311}$ is a substituted or unsubstituted aryl group having 6 to 60 ring carbon atoms or a substituted or unsubstituted heteroaryl group having 3 to 60 ring atoms, $Ar^{311'}$ is an arylene group having 6 to 60 ring carbon atoms or a substituted or unsubstituted heteroarylene group having 3 to 60 ring atoms, and $Ar^{312}$ is a hydrogen atom, a substituted or unsubstituted aryl group having 6 to 60 ring carbon atoms, a substituted or unsubstituted heteroaryl group having 3 to 60 ring atoms, a substituted or unsubstituted alkyl group having 1 to 20 carbon atoms, or a substituted or unsubstituted alkoxy group having 1 to 20 carbon atoms, provided that one of $Ar^{311}$ and $Ar^{312}$ is a substituted or unsubstituted fused ring group having 10 to 60 ring carbon atoms or a substituted or unsubstituted monohetero fused ring group having 3 to 60 ring atoms, $L^{311}$, $L^{312}$ and $L^{313}$ are independently a single bond, a substituted or unsubstituted arylene group having 6 to 60 ring carbon atoms, a substituted or unsubstituted heteroarylene group having 3 to 60 ring atoms, or a substituted or unsubstituted fluorenylene group, R and $R^{311}$ are independently a hydrogen atom, a substituted or unsubstituted aryl group having 6 to 60 ring carbon atoms, a substituted or unsubstituted heteroaryl group having 3 to 60 ring atoms, a substituted or unsubstituted alkyl group having 1 to 20 carbon atoms, or a substituted or unsubstituted alkoxy group having 1 to 20 carbon atoms, n is an integer of 0 to 5, and when n is two or more, plural Rs may be the same or different, and adjacent Rs may be bonded to each other to form a carbocyclic aliphatic ring or a carbocyclic aromatic ring.

$HAr-L^{314}-Ar^{321}—Ar^{322}$ (G)

Nitrogen-containing Heterocyclic Derivatives Shown by the Formula (G):
wherein HAr is a nitrogen-containing heterocyclic ring having 3 to 40 carbon atoms, which may have a substituent, $L^{314}$ is a single bond, an arylene group having 6 to 60 carbon atoms, which may have a substituent, an heteroarylene group having 3 to 60 atoms, which may have a substituent, or a fluorenylene group which may have a substituent, $Ar^{321}$ is a divalent aromatic hydrocarbon group having 6 to 60 carbon atoms, which may have a substituent, and $Ar^{322}$ is a an aryl group having 6 to 60 carbon atoms, which may have a substituent or a heteroaryl group having 3 to 60 atoms, which may have a substituent.

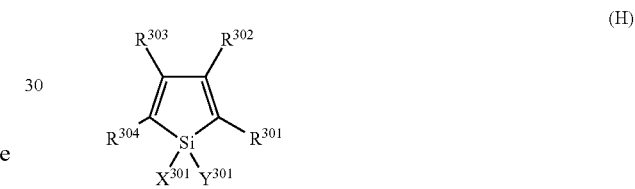

Silacyclopentadiene derivatives shown by the formula (H) wherein $X^{301}$ and $Y^{301}$ are independently a saturated or unsaturated hydrocarbon group having 1 to 6 carbon atoms, an alkoxy group, an alkenyloxy group, an alkynyloxy group, a hydroxyl group, a substituted or unsubstituted aryl group, or a substituted or unsubstituted hetero ring, or X and Y are bonded to form a saturated or unsaturated ring, and $R^{301}$ to $R^{304}$ are independently hydrogen, halogen, an alkyl group, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group. These groups may be substituted and adjacent groups may form a substituted or unsubstituted fused ring.

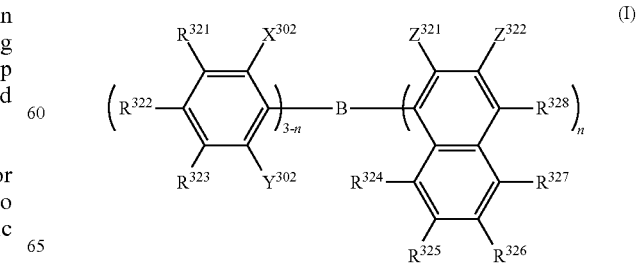

Borane derivatives shown by the formula (I) wherein $R^{321}$ to $R^{328}$ and $Z^{322}$ are independently a hydrogen atom, a saturated or unsaturated hydrocarbon group, an aromatic hydrocarbon group, a heterocyclic group, a substituted amino group, a substituted boryl group, an alkoxy group, or an aryloxy group, $X^{302}$, $Y^{302}$, and $Z^{321}$ are independently a saturated or unsaturated hydrocarbon group, an aromatic hydrocarbon group, a heterocyclic group, a substituted amino group, an alkoxy group, or an aryloxy group, $Z^{321}$ and $Z^{322}$ may be bonded to form a fused ring, and n is an integer of 1 to 3, provided that when n or (3-n) is two or more, $R^{321}$ to $R^{328}$, $X^{302}$, $Y^{302}$, $Z^{322}$ and $Z^{321}$ may be the same or different, provided that compounds where n is 1, $X^{302}$, $Y^{302}$, and $R^{322}$ are methyl groups, and $R^{328}$ is a hydrogen atom or a substituted boryl group, and compounds where n is 3 and $Z^{321}$ is a methyl group are excluded.

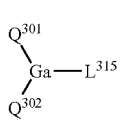

(J)

Gallium complexes shown by the formula (J) wherein $Q^{301}$ and $Q^{302}$ are independently ligands represented by the following formula (K) and $L^{315}$ is a halogen atom, a substituted or unsubstituted alkyl group, a substituted or unsubstituted cycloalkyl group, a substituted or unsubstituted aryl group, a substituted or unsubstituted heterocyclic group, —OR(R is a hydrogen atom, a substituted or unsubstituted alkyl group, a substituted or unsubstituted cycloalkyl group, a substituted or unsubstituted aryl group, or a substituted or unsubstituted heterocyclic group) or a ligand represented by —O—Ga—$Q^{303}(Q^{304})$ wherein $Q^{303}$ and $Q^{304}$ are the same as $Q^{301}$ and $Q^{302}$.

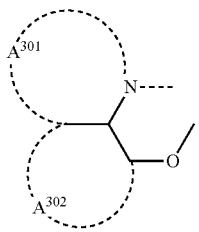

(K)

wherein rings $A^{301}$ and $A^{302}$ are independently a 6-membered aryl ring structure which may have a substituent and they are fused to each other.

The metal complexes have the strong nature of an n-type semiconductor and large ability of injecting electrons. Further, the energy generated at the time of forming a complex is small so that a metal is then strongly bonded to ligands in the complex formed and the fluorescent quantum efficiency becomes large as the emitting material.

Specific examples of the substituents for the rings $A^{301}$ and $A^{302}$ forming the ligand of the formula (K) include halogen atoms such as chlorine, bromine, iodine, and fluorine, substituted or unsubstituted alkyl groups such as a methyl group, ethyl group, propyl group, butyl group, sec-butyl group, tert-butyl group, pentyl group, hexyl group, heptyl group, octyl group, stearyl group, and trichloromethyl group, substituted or unsubstituted aryl groups such as a phenyl group, naphthyl group, biphenyl group, anthranyl group, phenanthryl group, fluorenyl group, pyrenyl group, 3-methylphenyl group, 3-methoxyphenyl group, 3-fluorophenyl group, 3-trichloromethylphenyl group, 3-trifluoromethylphenyl group, and 3-nitrophenyl group, substituted or unsubstituted alkoxy groups such as a methoxy group, n-butoxy group, tert-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, and 6-(perfluoroethyl)hexyloxy group, substituted or unsubstituted aryloxy groups such as a phenoxy group, p-nitrophenoxy group, p-tert-butylphenoxy group, 3-fluorophenoxy group, pentafluorophenoxy group, and 3-trifluoromethylphenoxy group, substituted or unsubstituted alkylthio groups such as a methylthio group, ethylthio group, tert-butylthio group, hexylthio group, octylthio group, and trifluoromethylthio group, substituted or unsubstituted arylthio groups such as a phenylthio group, p-nitrophenylthio group, p-tert-butylphenylthio group, 3-fluorophenylthio group, pentafluorophenylthio group, and 3-trifluoromethylphenylthio group, a cyano group, a nitro group, an amino group, mono- or di-substituted amino groups such as a methylamino group, dimethylamino group, ethylamino group, diethylamino group, dipropylamino group, dibutylamino group, and diphenylamino group, acylamino groups such as a bis(acetoxymethyl)amino group, bis(acetoxyethyl)amino group, bis(acetoxypropyl)amino group, and bis(acetoxybutyl)amino group, a hydroxyl group, a siloxy group, an acyl group, substituted or unsubstituted carbamoyl groups such as a carbamoyl group, methylcarbamoyl group, dimethylcarbamoyl group, ethylcarbamoyl group, diethylcarbamoyl group, propylcarbamoyl group, butylcarbamoyl group, and phenylcarbamoyl group, a carboxylic acid group, a sulfonic acid group, an imide group, cycloalkyl groups such as a cyclopentane group and cyclohexyl group, heterocyclic groups such as a pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholinyl group, piperazinyl group, carbazolyl group, furanyl group, thiophenyl group, oxazolyl group, oxadiazolyl group, benzoxazolyl group, thiazolyl group, thiadiazolyl group, benzothiazolyl group, triazolyl group, imidazolyl group, and benzimidazolyl group. The above substituents may be bonded to form a further six-membered aryl ring or heterocyclic ring.

A preferred embodiment of the organic EL device is a device containing a reducing dopant in an electron-transferring region or in an interfacial region between a cathode and an organic layer. The reducing dopant is defined as a substance which can reduce an electron-transferring compound. Accordingly, various substances which have given reducing properties can be used. For example, at least one substance can be preferably used which is selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, alkali metal carbonates, alkaline earth metal carbonates, rare earth metal carbonates, alkali metal organic complexes, alkaline earth metal organic complexes, and rare earth metal organic complexes.

More specific examples of the preferred reducing dopants include at least one alkali metal selected from the group consisting of Na (work function; 2.36 eV), K (work function: 2.28 eV), Rb (work function: 2.16 eV) and Cs (work function: 1.95 eV), and at least one alkaline earth metal selected from the group consisting of Ca (work function: 2.9 eV), Sr (work function: 2.0 to 2.5 eV), and Ba (work function: 2.52 eV). Metals having a work function of 2.9 eV or less are particularly preferred. Among these, a more preferable reducing dopant is at least one alkali metal selected from the group consisting of K, Rb and Cs. Even more preferable is Rb or Cs. Most preferable is Cs. These alkali metals are particularly high in reducing ability. Thus, the addition of a relatively small amount thereof to an electron-injecting zone improves the luminance of the organic EL device and make the lifetime thereof long. As a reducing agent having a work function of 2.9 eV or less, combinations of two or more alkali metals are preferable, particularly combinations including Cs, such as Cs and Na, Cs and K, Cs and Rb, or Cs, Na and K are preferable. The combination containing Cs makes it possible to exhibit the reducing ability efficiently. The luminance of the organic EL device can be improved and the lifetime thereof can be made long by the addition thereof to its electron-injecting zone.

An electron-injecting layer made of an insulator or a semiconductor may further be provided between a cathode and an organic layer. By forming the electron-injecting layer, a current leakage can be effectively prevented and electron-injecting properties can be improved. If the electron-injecting layer is an insulating thin film, more uniformed thin film can be formed whereby pixel defects such as a dark spot are decreased.

As the insulator, at least one metal compound selected from the group consisting of alkali metal calcogenides, alkaline earth metal calcogenides, halides of alkali metals and halides of alkaline earth metals can be preferably used. When the electron-injecting layer is formed of the alkali metal calcogenide or the like, the injection of electrons can be preferably further improved. Specifically preferable alkali metal calcogenides include $Li_2O$, $K_2O$, $Na_2S$, $Na_2Se$ and $Na_2O$ and preferable alkaline earth metal calcogenides include CaO, BaO, SrO, BeO, BaS and CaSe. Preferable halides of alkali metals include LiF, NaF, KF, CsF, LiCl, KCl and NaCl. Preferable halides of alkaline earth metals include fluorides such as $CaF_2$, $BaF_2$, $SrF_2$, $MgF_2$ and $BeF_2$ and the other halides corresponding to the fluorides.

Semiconductors forming an electron-injecting layer include one or combinations of two or more of oxides, nitrides, and oxidized nitrides containing at least one element of Ba, Ca, Sr, Yb, Al, Ga, In, Li, Na, Cd, Mg, Si, Ta, Sb and Zn. An inorganic compound forming an electron-injecting layer is preferably a microcrystalline or amorphous insulating thin film.

For the cathode, the following may be used: an electrode substance made of a metal, an alloy or an electroconductive compound, or a mixture thereof which has a small work function (for example, 4 eV or less). Specific examples of the electrode substance include sodium, sodium-potassium alloy, magnesium, lithium, cesium, magnesium/silver alloy, aluminum/aluminum oxide, $Al/Li_2O$, Al/LiO, Al/LiF, aluminum/lithium alloy, indium, and rare earth metals.

The cathode is formed from these electrode materials by vapor deposition, sputtering or the like.

In the case where emission from the emitting layer is outcoupled through the cathode, it is preferred to make the transmittance of the cathode to the emission larger than 10%. The sheet resistance of the cathode is preferably several hundreds $\Omega/\square$ or less, and the film thickness thereof is usually from 10 nm to 1 μm, preferably from 50 to 200 nm.

Generally, in the organic EL device, pixel defects based on leakage or a short circuit are easily generated since an electric field is applied to the super thin film. In order to prevent this, it is preferred to insert an insulating thin layer between the pair of electrodes.

Examples of the material used in the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or laminate thereof may be used.

As for the method for fabricating the organic EL device, it can be fabricated by forming necessary layers sequentially from the anode using the materials and the method as mentioned above, and finally forming the cathode. The organic EL device can be fabricated in the order reverse to the above, i.e., the order from the cathode to the anode.

An example of the fabrication of the organic EL device will be described below which has a structure wherein the following are successively formed on a transparent substrate: anode/hole-injecting layer/emitting layer/electron-injecting layer/cathode.

At first, a thin film formed of an anode material is formed on a transparent substrate by vapor deposition or sputtering to form an anode.

Next, a hole-injecting layer is formed on this anode. As described above, the hole-injecting layer can be formed by vacuum deposition, spin coating, casting, LB technique, or some other method. Vacuum deposition is preferred since a homogenous film is easily obtained and pinholes are not easily generated. In the case where the hole-injecting layer is formed by vacuum deposition, conditions for the deposition vary depending upon a compound used (a material for the hole-injecting layer), a desired structure of the hole-injecting layer, and others. In general, the conditions are preferably selected from the following: deposition source temperature of 50 to 450° C., vacuum degree of $10^{-7}$ to $10^{-3}$ Torr, vapor deposition rate of 0.01 to 50 nm/second, and substrate temperature of −50 to 300° C.

Next, an emitting layer is formed on the hole-injecting layer. The emitting layer can also be formed by making a luminescent material into a thin film by vacuum vapor deposition, sputtering, spin coating, casting or some other method. Vacuum vapor deposition is preferred since a homogenous film is easily obtained and pinholes are not easily generated. In the case where the emitting layer is formed by vacuum vapor deposition, conditions for the deposition, which vary depending on a compound used, can be generally selected from conditions similar to those for the hole-injecting layer.

Next, an electron-injecting layer is formed on the emitting layer. Like the hole-injecting layer and the emitting layer, the layer is preferably formed by vacuum vapor deposition because a homogenous film is required. Conditions for the deposition can be selected from conditions similar to those for the hole-injecting layer and the emitting layer.

Lastly, a cathode is stacked thereon to obtain an organic EL device. The cathode can be formed by vapor deposition or sputtering. However, vapor vacuum deposition is preferred in order to protect underlying organic layers from being damaged when the cathode film is formed.

For the organic EL device fabrication described above, it is preferred that the formation from the anode to the cathode is continuously carried out, using only one vacuuming operation.

The method for forming each of the layers in the organic EL device is not particularly limited. An organic thin film layer containing the compound of the invention can be formed by a known method such as vacuum vapor deposition, molecular beam epitaxy (MBE), or an applying coating method using a solution in which the compound is dissolved in a solvent, such as dipping, spin coating, casting, bar coating, or roll coating.

EXAMPLES

Examples will be explained below. However, the invention is not limited by these examples.

Organic EL devices were evaluated as follows:
(1) Initial performance: Luminance and CIE1931 chromaticity coordinate at 10 mA/cm$^2$ were measured by a luminance meter (Spectroradiometer CS-1000 manufactured by Minorta Co., Ltd.) and luminous efficiency was then obtained.
(2) Life time: The organic EL device is driven at a constant current with an initial luminance of 1000 cd/m$^2$, and life time thereof was evaluated with the half-life of luminance and variation in chromaticity.

Example 1

(1) Synthesis of Benzanthracene Compound

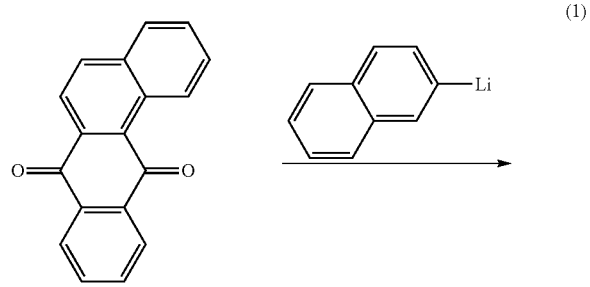

(1)

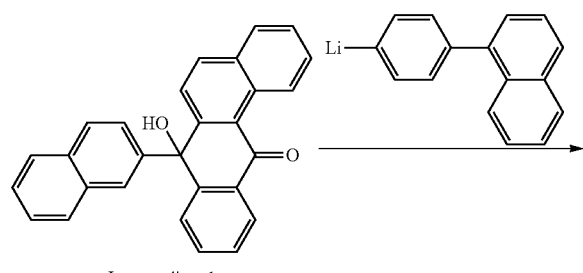

Intermediate 1

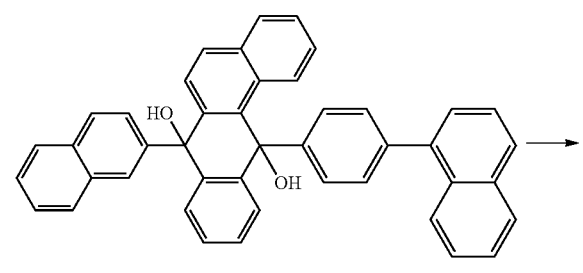

Intermediate 2

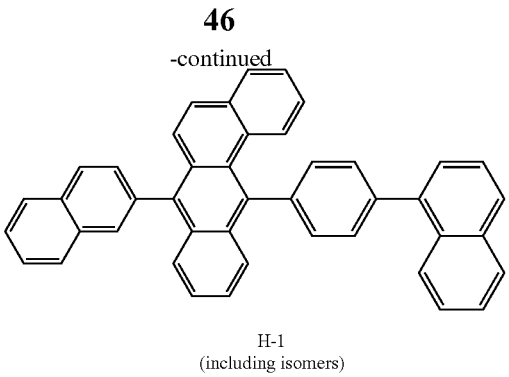

H-1
(including isomers)

To a 1 L four-necked flask, 8.28 g (40.0 mmol) of 2-bromonaphthalene was placed, and argon substitution was conducted by repeating three times decrease of pressure in the system and returning it to the original pressure with argon gas. Subsequently, 60 mL of dried tetrahydrofuran was added and stirred to completely dissolve it in the reaction solution, followed by cooling to about −65° C. with a dry ice/acetone bath. To the reaction solution, 25 mL (40.0 mmol) of a solution of 1.57M of n-butyl lithium in hexane was dropwise added for about 20 minutes. After the reaction was continued at −65° C. for 2 hours, a solution of 10.3 g (40.0 mmol) of benzanthraquinone in 150 mL of dried tetrahydrofuran was dropwise added for 30 minutes. Then, the reaction was conducted at −65° C. for about 2 hours, the temperature was increased to room temperature, and the reaction was continued for 2 hours. Next day, 50 mL of 1N hydrochloric acid was added to terminate the reaction. Subsequently, the reaction solution was extracted with ethyl acetate/water. Na$_2$SO$_4$ was added to the organic phase, stirred for one hour and dried, and then concentrated. To the resultant solids, 50 mL of a solution of hexane/ethyl acetate=1/1 was added, precipitants were collected by filtration and dried in vacuo (Intermediate 1: yield amount: 12.4 g, yield: 80.0%, HPLC purity: 98.3%).

To a 1 L flask, 9.06 g (32 mmol) of 1-(4-bromo-phenyl)-naphthalene was placed, and argon substitution was conducted by repeating three times decrease of pressure in the system and returning it to the original pressure with argon gas. Subsequently, 60 mL of dried tetrahydrofuran was added, stirred to completely dissolve it in the reaction solution. The reaction solution was cooled to about −65° C. with a dry ice/acetone bath, and 20 mL (32.0 mmol) of a solution of 1.57M n-butyl lithium in hexane was dropwise added for about 20 minutes. After the reaction was continued at −65° C. for 2 hours, a solution of 12.4 g (32.0 mmol) of Intermediate 1 in 150 mL of dried tetrahydrofuran was dropwise added for 30 minutes. Then, the reaction was conducted at −65° C. for about 2 hours, the temperature of the reaction solution was increased to room temperature, and the reaction was conducted for 2 hours. Next day, 50 mL of 1N hydrochloric acid was added to terminate the reaction, and then the reaction solution was extracted with ethyl acetate/water. Na$_2$SO$_4$ was added to the organic phase, stirred for one hour and dried, and concentrated. To resultant solids, 50 mL of a solution of hexane/ethyl acetate=1/1 was added, precipitates were collected by filtration and dried in vacuo (Intermediate 2: yield amount: 14.8 g, yield: 78.1%, HPLC purity: 99.3%).

To a 1 L flask, 14.8 g (25.1 mmol) of Intermediate 2, 10.4 g (62.8 mmol) of potassium iodide and 3.33 g (31.4 mmol) of NaPH$_2$O$_2$.H$_2$O were placed, substitution in the system was conducted with argon gas, and 300 mL of acetic acid was added to the mixture. Subsequently, the reaction solution was heated with an oil bath and reacted at 80° C. for 8 hours. Next day, precipitants were collected by filtration, washed with acetic acid, methanol and water, and then dried in vacuo to obtain Compound H-1 (yield amount: 8.57 g, yield: 61.3%).

Subsequently, halogen content was reduced in accordance with the method disclosed in JP-A-2007-77078 (yield amount: 6.52 g, HPLC purity: 99.9%, FD-MS: 556.69).

(2) Fabrication of Organic EL Device

A glass substrate of 25 mm by 75 mm by 1.1 mm thick with an ITO transparent electrode (anode) (GEOMATEC CO., LTD.) was subjected to ultrasonic cleaning with isopropyl alcohol for 5 minutes, and then cleaned with ultraviolet rays and ozone for 30 minutes. The cleaned glass substrate with transparent electrode lines was mounted in a substrate holder of a vapor deposition apparatus. First, as a hole injecting layer, a 60 nm-thick film of the following compound A-1 was formed on the surface where the transparent electrode lines were formed so as to cover the transparent electrode. Subsequent to the film formation of A-1 film, a 20 nm-thick film of the following compound A-2 was formed on the A-1 film, as a hole transporting layer.

A 40 nm-thick film was formed on the A-2 film using compound H-1 of the invention and a diamine derivative D-1 in a film thickness ratio of 40:2, to obtain a blue-light emitting layer. H-1 acts as a host and D-1 acts as a do pant.

On this film, a 20 nm-thick film was formed as an electron transporting layer using the following compound Alq by deposition, followed by formation of 1 nm-thick LiF film. A 150 nm-thick metal Al film was formed on the LiF film by deposition to form a metal cathode, whereby an organic EL device was obtained.

A-1

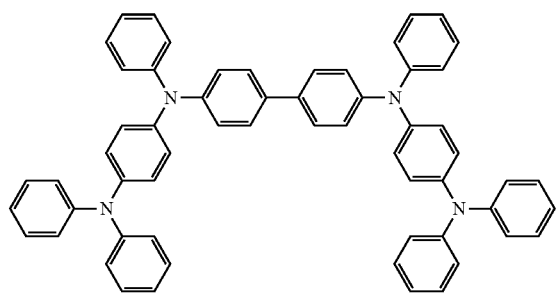

A-2

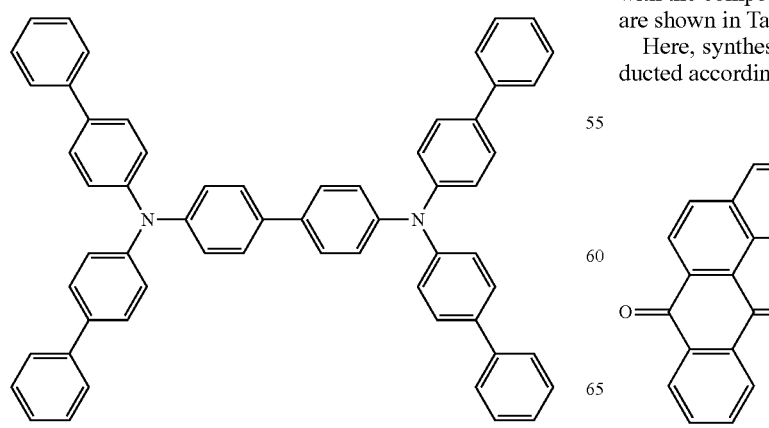

D-1

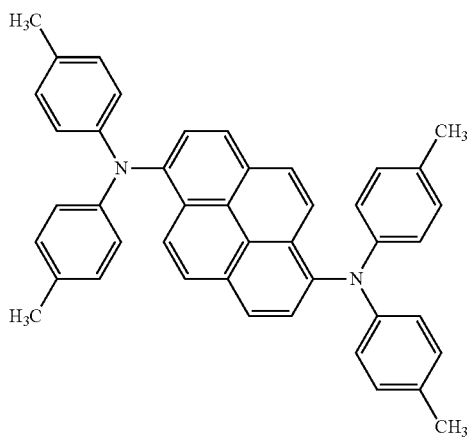

Alq

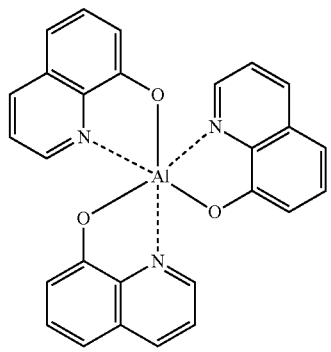

For the organic EL devices fabricated, initial performances (chromaticity and luminous efficiency) and half life (time) were evaluated. The results are shown in Table 1. From Table 1, it is understood that light emission superior in blue chromaticity could be obtained.

Examples 2 to 39

A device was fabricated and evaluated in the same manner as in Example 1 except that H-1 and/or D-1 were replaced with the compounds indicated in Tables 1 and 2. The results are shown in Tables 1 and 2.

Here, synthesis of benzanthracene compounds were conducted according to the synthesis routes (2) to (4).

(2)

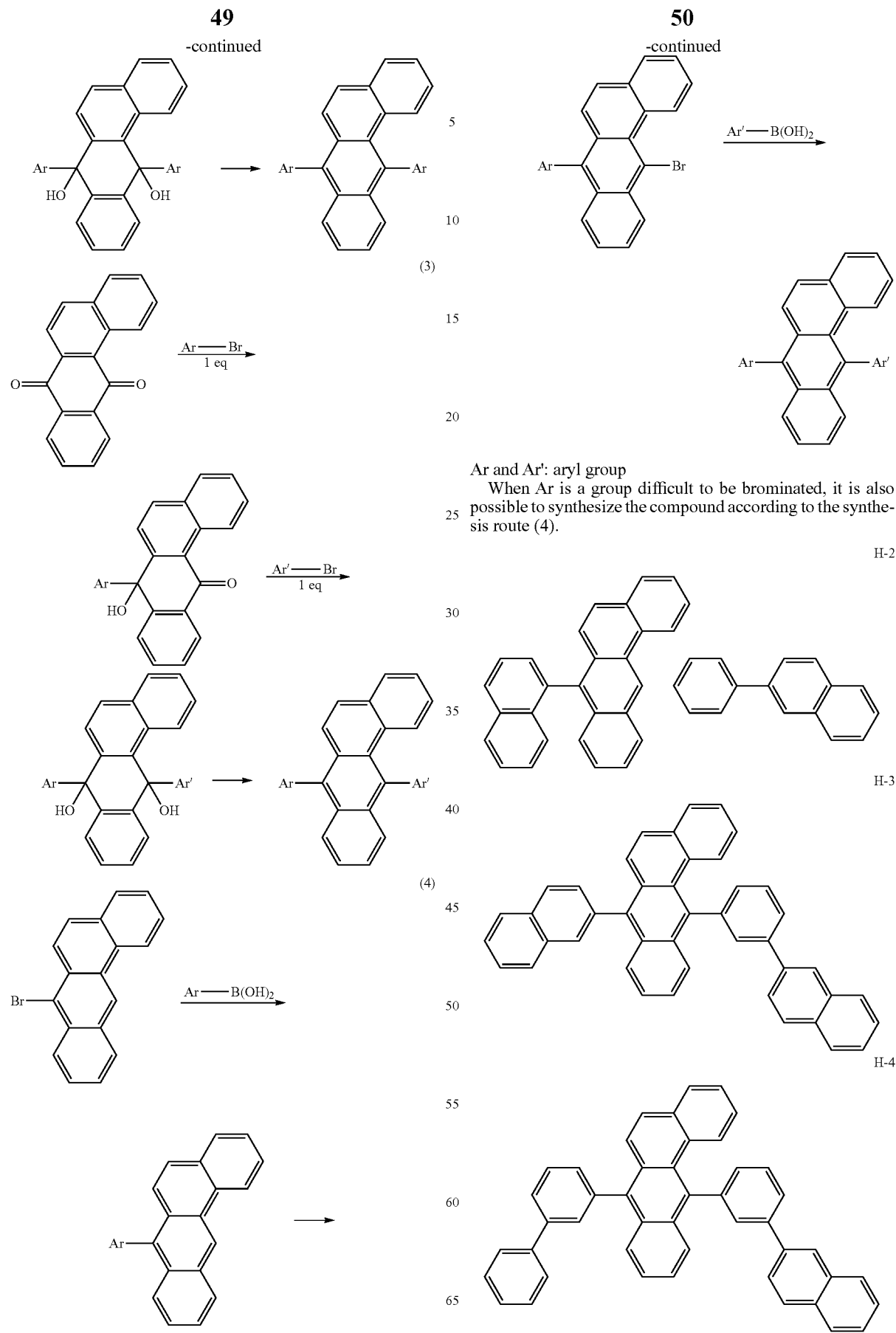
Ar and Ar': aryl group
When Ar is a group difficult to be brominated, it is also possible to synthesize the compound according to the synthesis route (4).

H-5
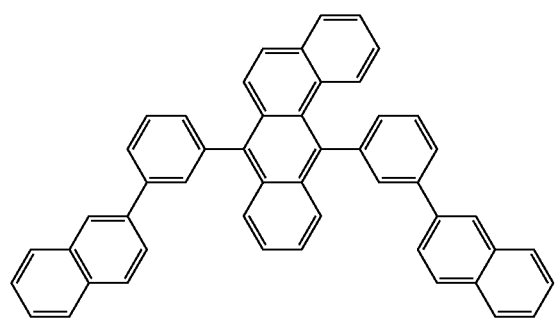
H-6
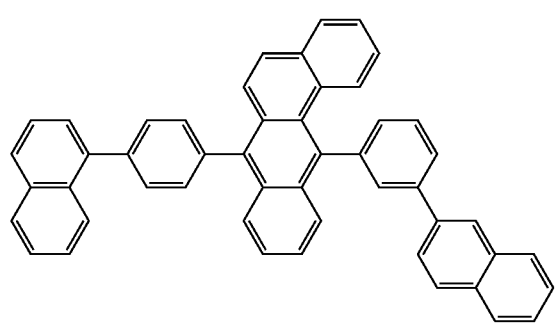
H-7
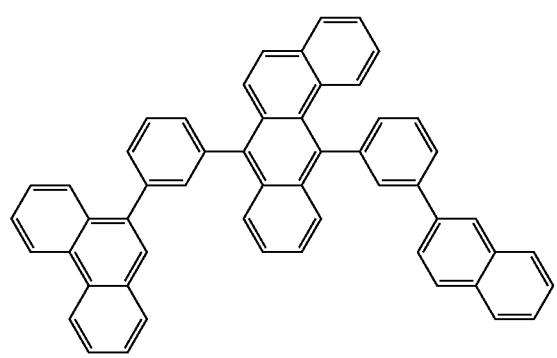
H-8
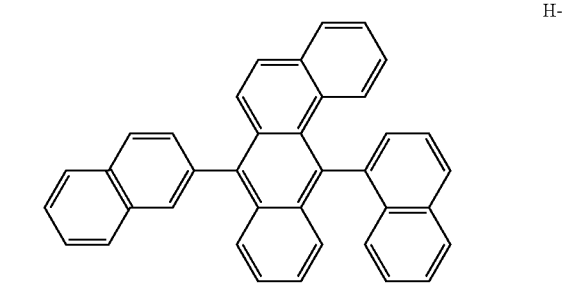
H-9
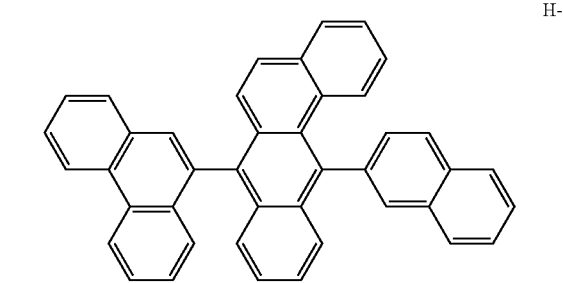
H-10
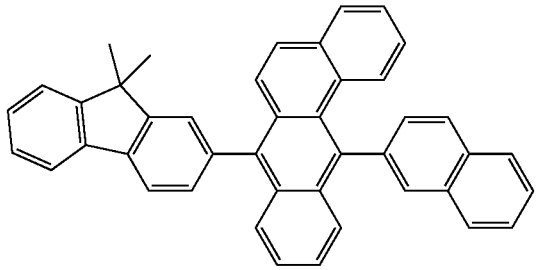
H-11
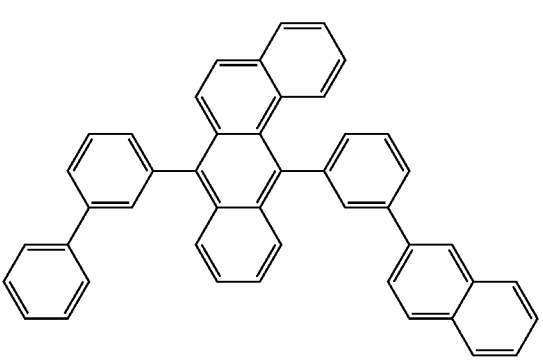
(synthesized according to synthesis route (4), no isomer)
H-12
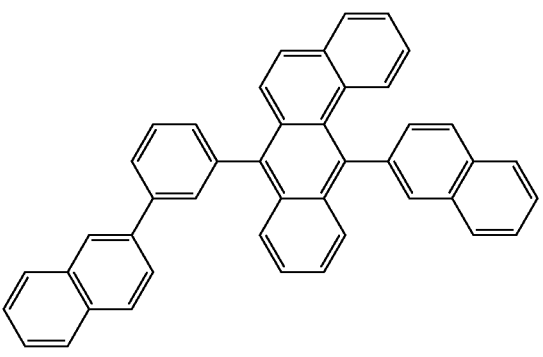
(synthesized according to synthesis route (4), no isomer)
H-13
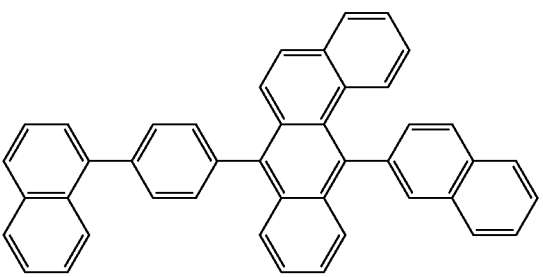
(synthesized according to synthesis route (4), no isomer)

-continued

D-2

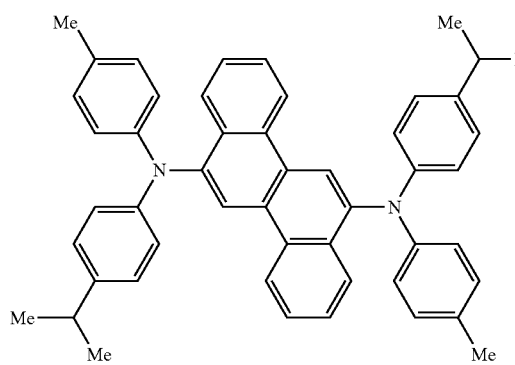

D-3

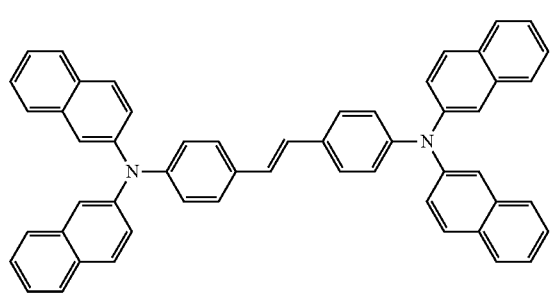

Comparative Examples 1 to 3

(1) Synthesis of Benzanthracene Compound

Synthesis was conducted according to a conventional method in the same manner as in Example 1.

h-1

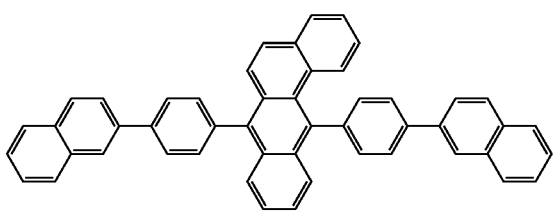

h-2

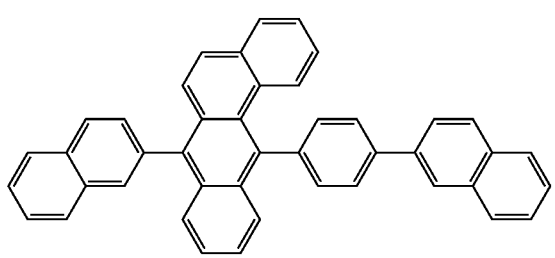

-continued h-3

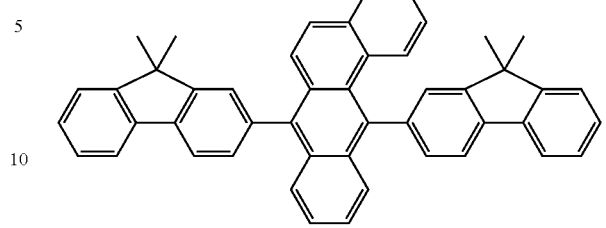

(2) Fabrication of Organic EL Device

A device was fabricated in the same manner as in Example 1 except that H-1 and D-1 were replaced with the compounds indicated in Table 2. The results are shown in Table 2.

TABLE 1

| | Emitting material | | Chromaticity | Luminous efficiency | Half life (hour) |
|---|---|---|---|---|---|
| | (Host) | (Dopant) | (CIEx, CIEy) | (cd/A) | @1000 cd/m$^2$ |
| Ex. 1 | H-1 | D-1 | (0.15, 0.19) | 7.9 | 8,900 |
| Ex. 2 | H-1 | D-2 | (0.16, 0.18) | 8.2 | 9,200 |
| Ex. 3 | H-1 | D-3 | (0.15, 0.17) | 7.0 | 8,200 |
| Ex. 4 | H-2 | D-1 | (0.14, 0.18) | 7.8 | 8,700 |
| Ex. 5 | H-2 | D-2 | (0.15, 0.19) | 8.1 | 8,900 |
| Ex. 6 | H-2 | D-3 | (0.15, 0.16) | 7.1 | 8,100 |
| Ex. 7 | H-3 | D-1 | (0.14, 0.18) | 8.0 | 9,100 |
| Ex. 8 | H-3 | D-2 | (0.16, 0.18) | 8.2 | 8,800 |
| Ex. 9 | H-3 | D-3 | (0.15, 0.16) | 7.1 | 8,100 |
| Ex. 10 | H-4 | D-1 | (0.14, 0.17) | 7.6 | 8,300 |
| Ex. 11 | H-4 | D-2 | (0.16, 0.19) | 8.3 | 8,500 |
| Ex. 12 | H-4 | D-3 | (0.15, 0.15) | 7.0 | 7,800 |
| Ex. 13 | H-5 | D-1 | (0.14, 0.17) | 8.4 | 9,000 |
| Ex. 14 | H-5 | D-2 | (0.15, 0.18) | 7.7 | 7,900 |
| Ex. 15 | H-5 | D-3 | (0.15, 0.16) | 7.5 | 8,500 |
| Ex. 16 | H-6 | D-1 | (0.14, 0.17) | 8.3 | 8,900 |
| Ex. 17 | H-6 | D-2 | (0.15, 0.18) | 8.1 | 8,600 |
| Ex. 18 | H-6 | D-3 | (0.15, 0.16) | 7.3 | 8,400 |
| Ex. 19 | H-7 | D-1 | (0.14, 0.17) | 7.0 | 8,200 |
| Ex. 20 | H-7 | D-2 | (0.16, 0.16) | 7.3 | 8,000 |

TABLE 2

| | Emitting material | | Chromaticity | Luminous efficiency | Half life (hour) |
|---|---|---|---|---|---|
| | (Host) | (Dopant) | (CIEx, CIEy) | (cd/A) | @1000 cd/m$^2$ |
| Ex. 21 | H-7 | D-3 | (0.15, 0.16) | 7.1 | 8,100 |
| Ex. 22 | H-8 | D-1 | (0.14, 0.16) | 7.8 | 8,300 |
| Ex. 23 | H-8 | D-2 | (0.16, 0.17) | 7.6 | 8,200 |
| Ex. 24 | H-8 | D-3 | (0.15, 0.15) | 7.1 | 8,000 |
| Ex. 25 | H-9 | D-1 | (0.14, 0.17) | 7.8 | 8,600 |
| Ex. 26 | H-9 | D-2 | (0.16, 0.18) | 7.5 | 7,800 |
| Ex. 27 | H-9 | D-3 | (0.15, 0.16) | 7.1 | 8,100 |
| Ex. 28 | H-10 | D-1 | (0.14, 0.17) | 7.4 | 8,600 |
| Ex. 29 | H-10 | D-2 | (0.16, 0.18) | 7.2 | 8,000 |
| Ex. 30 | H-10 | D-3 | (0.15, 0.16) | 7.1 | 8,000 |
| Ex. 31 | H-11 | D-1 | (0.14, 0.15) | 7.3 | 7,100 |
| Ex. 32 | H-11 | D-2 | (0.16, 0.17) | 7.4 | 7,700 |
| Ex. 33 | H-11 | D-3 | (0.15, 0.15) | 7.1 | 7,300 |
| Ex. 34 | H-12 | D-1 | (0.14, 0.17) | 8.2 | 8,700 |
| Ex. 35 | H-12 | D-2 | (0.16, 0.17) | 8.1 | 8,800 |
| Ex. 36 | H-12 | D-3 | (0.15, 0.15) | 7.3 | 7,800 |
| Ex. 37 | H-13 | D-1 | (0.14, 0.16) | 7.6 | 8,400 |
| Ex. 38 | H-13 | D-2 | (0.16, 0.16) | 7.8 | 8,300 |

TABLE 2-continued

|  | Emitting material | | Chromaticity | Luminous efficiency | Half life (hour) |
|---|---|---|---|---|---|
|  | (Host) | (Dopant) | (CIEx, CIEy) | (cd/A) | @1000 cd/m$^2$ |
| Ex. 39 | H-13 | D-3 | (0.15, 0.15) | 7.1 | 8,100 |
| Comp. Ex. 1 | h-1 | D-2 | (0.20, 0.29) | 5.9 | 3,000 |
| Comp. Ex. 2 | h-2 | D-2 | (0.21, 0.35) | 5.5 | 2,800 |
| Comp. Ex. 3 | h-3 | D-2 | (0.20, 0.31) | 5.3 | 2,000 |

As understood from Tables 1 and 2, when the compound of the invention is used as the emitting material, blue light emission having good chromaticity can be obtained, and the half life of the device becomes longer than that of the device using a conventional compound.

Examples 40 to 45 and Comparative Examples 4 to 6

An organic EL device was fabricated in the same manner as in Example 1 except that a dopant material and a host material of the emitting layer were replaced with compounds indicated in Table 3. Table 3 shows the results.

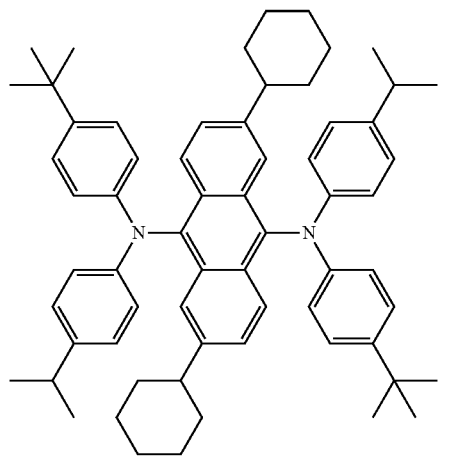
D-4

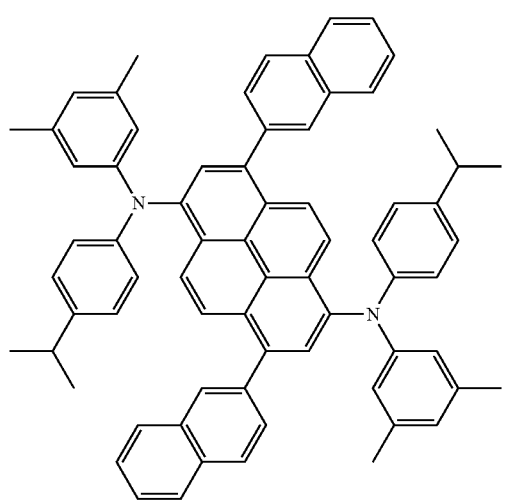
D-5

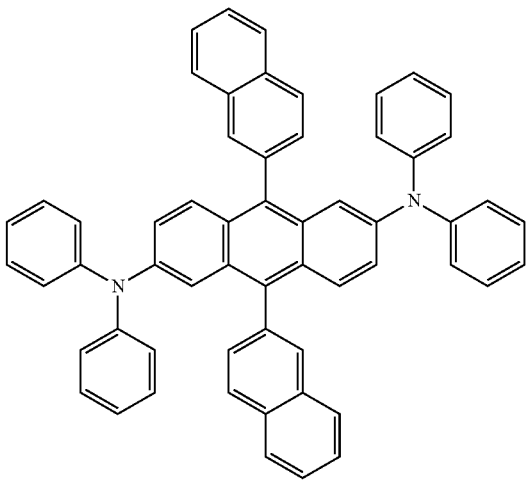
D-6

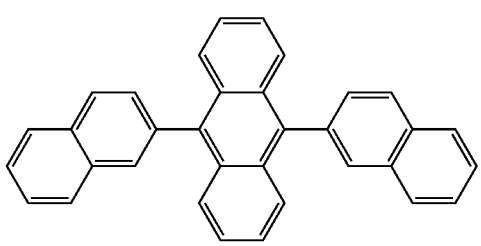
h-4

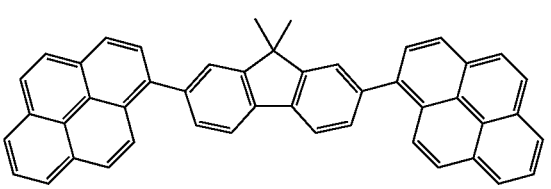
h-5

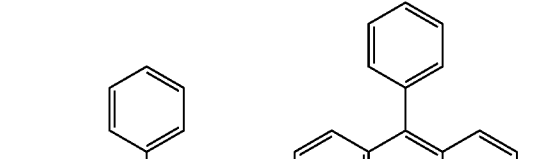
h-6

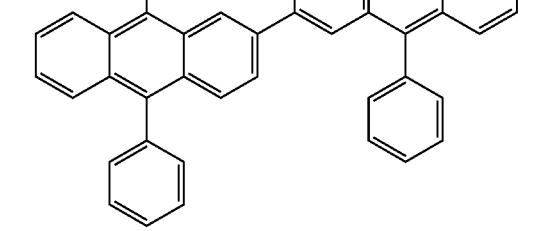

TABLE 3

|  | Emitting material | | Chromaticity | Luminous efficiency | Half life (hour) |
|---|---|---|---|---|---|
|  | (Host) | (Dopant) | (CIEx, CIEy) | (cd/A) | @5000 cd/m$^2$ |
| Ex. 40 | H-8 | D-4 | (0.333, 0.618) | 25.2 | 11300 |
| Ex. 41 | H-8 | D-5 | (0.280, 0.633) | 23.3 | 12800 |
| Ex. 42 | H-8 | D-6 | (0.319, 0.634) | 23.4 | 11600 |
| Ex. 43 | H-12 | D-4 | (0.334, 0.618) | 26.2 | 12500 |

TABLE 3-continued

| | Emitting material | | Chromaticity | Luminous efficiency | Half life (hour) |
|---|---|---|---|---|---|
| | (Host) | (Dopant) | (CIEx, CIEy) | (cd/A) | @5000 cd/m$^2$ |
| Ex. 44 | H-12 | D-5 | (0.285, 0.638) | 24.5 | 12600 |
| Ex. 45 | H-12 | D-6 | (0.321, 0.635) | 24.3 | 11900 |
| Comp. Ex. 4 | h-4 | D-6 | (0.319, 0.640) | 17.9 | 5200 |
| Comp. Ex. 5 | h-5 | D-6 | (0.313, 0.636) | 18.5 | 3400 |
| Comp. Ex. 6 | h-6 | D-6 | (0.313, 0.633) | 18.5 | 3800 |

As understood from Table 3, when the compound of the invention is used as an emitting material, green light emission having high color purity can be also obtained, and the half life of the device becomes longer than that of the device using a conventional compound.

INDUSTRIAL APPLICABILITY

The benzanthracene compound of the invention can be used as an emitting material for an organic EL device.

The organic EL device of the invention can be suitably used as a light source such as a planar emitting body and backlight of a display, a display part of a portable phone, a PDA, a car navigator, or an instrument panel of an automobile, an illuminator, and the like.

The documents described in the specification are incorporated herein by reference in its entirety.

The invention claimed is:

1. An organic electroluminescence device which comprises: an anode, a cathode, and one or more organic thin film layers including an emitting layer, which are between the anode and the cathode, wherein at least one layer of the organic thin film layers comprises a compound represented by the following formula (1) or (1)':

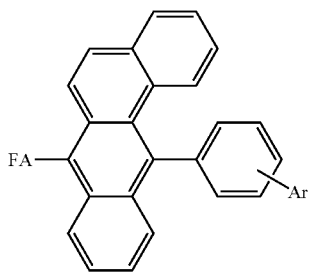
(1)

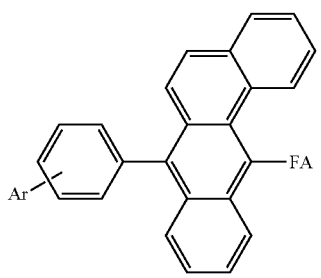
(1)' wherein FA is a fused aromatic ring, and Ar is an aromatic group and wherein the layer comprising the compound further comprises at least one of a phosphorescent dopant and a fluorescent dopant.

2. An emitting material comprising the compound according to claim 1.

3. The organic electroluminescence device according to claim 1, wherein the fluorescent dopant is at least one of arylamine compounds and styrylamine compounds.

4. The organic electroluminescence device according to claim 1, wherein the phosphorescent dopant is a metal complex.

* * * * *